US011235141B2

(12) United States Patent
Lucke et al.

(10) Patent No.: US 11,235,141 B2
(45) Date of Patent: Feb. 1, 2022

(54) DATA COMMUNICATION IN A TRANSCUTANEOUS ENERGY TRANSFER SYSTEM

(71) Applicant: Minnetronix, Inc., St. Paul, MN (US)

(72) Inventors: Lori Lucke, Rosemount, MN (US); Vlad Bluvshtein, Plymouth, MN (US); James Kurkowski, Roseville, MN (US); William Weiss, Mechanicsburg, PA (US)

(73) Assignee: Minnetronix, Inc., St. Paul, MN (US)

( * ) Notice: Subject to any disclaimer, the term of this patent is extended or adjusted under 35 U.S.C. 154(b) by 80 days.

(21) Appl. No.: 16/564,210

(22) Filed: Sep. 9, 2019

(65) Prior Publication Data

US 2020/0000990 A1    Jan. 2, 2020

Related U.S. Application Data

(62) Division of application No. 14/995,962, filed on Jan. 14, 2016, now Pat. No. 10,406,267.
(Continued)

(51) Int. Cl.
*A61M 60/871* (2021.01)
*H04B 3/54* (2006.01)
(Continued)

(52) U.S. Cl.
CPC ......... *A61M 60/871* (2021.01); *A61N 1/3727* (2013.01); *A61N 1/3787* (2013.01);
(Continued)

(58) Field of Classification Search
CPC ............... A61M 60/871; A61N 1/3787; A61N 1/37223; A61N 1/3727
See application file for complete search history.

(56) References Cited

U.S. PATENT DOCUMENTS

| 3,195,540 A | 7/1965 | Waller |
| 3,566,876 A | 3/1971 | Stoft et al. |

(Continued)

FOREIGN PATENT DOCUMENTS

| DE | 102006037668 A1 | 3/2007 |
| DE | 102015112097 A1 | 1/2016 |

(Continued)

OTHER PUBLICATIONS

"Modulator (in German)", Wikipedia Version 20130328.
(Continued)

*Primary Examiner* — George R Evanisko
(74) *Attorney, Agent, or Firm* — Seager, Tufte & Wickhem LLP

(57) ABSTRACT

Disclosed are systems and methods for use of an inductive link for a communication channel in a transcutaneous energy transfer system. An example system may include a resonant circuit associated with an external primary, a power transistor connected to the resonant circuit and configured to drive the resonant circuit with a first time-varying electrical signal having a frequency, and a power driver connected to the power transistor that is configured to set the frequency of the first time-varying electrical signal to a resonant frequency to enable power transfer from the external primary to an implanted secondary. The example system may further include a communication driver operatively connected to the power transistor and configured to encode the first time-varying electrical signal with a data signal by modulating an attribute of the time-varying electrical signal as electrical power is transferred from the external primary to the implanted secondary.

13 Claims, 11 Drawing Sheets

Related U.S. Application Data

(60) Provisional application No. 62/104,451, filed on Jan. 16, 2015.

(51) Int. Cl.
  *A61N 1/378* (2006.01)
  *A61N 1/372* (2006.01)
  *A61M 60/148* (2021.01)
  *A61M 60/205* (2021.01)

(52) U.S. Cl.
  CPC ......... *A61N 1/37223* (2013.01); *H04B 3/54* (2013.01); *H04B 3/548* (2013.01); *A61M 60/148* (2021.01); *A61M 60/205* (2021.01)

(56) References Cited

U.S. PATENT DOCUMENTS

| | | |
|---|---|---|
| 3,756,246 A | 9/1973 | Thaler et al. |
| 3,760,332 A | 9/1973 | Berkovits et al. |
| 3,806,807 A | 4/1974 | Nakamura |
| 3,943,535 A | 3/1976 | Schulman |
| 4,082,097 A | 4/1978 | Mann et al. |
| 4,143,661 A | 3/1979 | LaForge et al. |
| 4,164,946 A | 8/1979 | Langer |
| 4,221,543 A | 9/1980 | Cosentino et al. |
| 4,233,546 A | 11/1980 | Berthiaume |
| 4,237,895 A | 12/1980 | Johnson |
| 4,263,642 A | 4/1981 | Simmons et al. |
| 4,361,153 A | 11/1982 | Slocum et al. |
| 4,417,349 A | 11/1983 | Hills et al. |
| 4,439,806 A | 3/1984 | Brajder |
| 4,441,210 A | 4/1984 | Hochmair et al. |
| 4,446,513 A | 5/1984 | Clenet |
| 4,453,537 A | 6/1984 | Spitzer |
| 4,469,104 A | 9/1984 | Peers-Trevarton |
| 4,494,545 A | 1/1985 | Slocum et al. |
| 4,532,932 A | 8/1985 | Batty, Jr. |
| 4,561,443 A | 12/1985 | Hogrefe et al. |
| 4,625,730 A | 12/1986 | Fountain et al. |
| 4,665,896 A | 5/1987 | LaForge et al. |
| 4,681,111 A | 7/1987 | Silvian |
| 4,691,270 A | 9/1987 | Pruitt |
| 4,706,689 A | 11/1987 | Man |
| 4,768,512 A | 9/1988 | Imran |
| 4,774,950 A | 10/1988 | Cohen |
| 4,848,346 A | 7/1989 | Crawford |
| 4,855,888 A | 8/1989 | Henze et al. |
| 4,898,173 A | 2/1990 | Daglow et al. |
| 4,924,171 A | 5/1990 | Baba et al. |
| 4,925,443 A | 5/1990 | Heilman et al. |
| 4,933,798 A | 6/1990 | Widmayer et al. |
| 4,941,652 A | 6/1990 | Nagano et al. |
| 4,941,201 A | 7/1990 | Davis |
| 4,947,844 A | 8/1990 | McDermott |
| 4,953,068 A | 8/1990 | Henze |
| 4,964,027 A | 10/1990 | Cook et al. |
| 4,979,506 A | 12/1990 | Silvian |
| 5,012,807 A | 5/1991 | Stutz, Jr. |
| 5,076,270 A | 12/1991 | Stutz, Jr. |
| 5,132,888 A | 7/1992 | Lo et al. |
| 5,132,889 A | 7/1992 | Hitchcock et al. |
| 5,157,593 A | 10/1992 | Jain |
| 5,158,097 A | 10/1992 | Christlieb |
| 5,205,810 A | 4/1993 | Guiraudon et al. |
| 5,279,292 A | 1/1994 | Baumann et al. |
| 5,314,457 A * | 5/1994 | Jeutter .................. A61N 1/372 128/903 |
| 5,327,335 A | 7/1994 | Maddali et al. |
| 5,345,375 A | 9/1994 | Mohan |
| 5,350,413 A | 9/1994 | Miller |
| 5,400,235 A | 3/1995 | Carroll |
| 5,413,595 A | 5/1995 | Stutz, Jr. |
| 5,438,498 A | 8/1995 | Ingemi |
| 5,444,608 A | 8/1995 | Jain |
| 5,456,715 A | 10/1995 | Liotta |
| 5,499,178 A | 3/1996 | Mohan |
| 5,500,004 A | 3/1996 | Ansourian et al. |
| 5,515,264 A | 5/1996 | Stacey |
| 5,522,865 A | 6/1996 | Schuman et al. |
| 5,559,689 A | 9/1996 | Kirchberg et al. |
| 5,569,156 A | 10/1996 | Mussivand |
| 5,569,307 A | 10/1996 | Schulman et al. |
| 5,584,870 A | 12/1996 | Single et al. |
| 5,594,635 A | 1/1997 | Gegner |
| 5,630,836 A | 5/1997 | Prem et al. |
| 5,662,692 A | 9/1997 | Paspa et al. |
| 5,674,281 A | 10/1997 | Snyder |
| 5,690,693 A | 11/1997 | Wang et al. |
| 5,702,427 A | 12/1997 | Ecker et al. |
| 5,702,431 A | 12/1997 | Wang et al. |
| 5,704,891 A | 1/1998 | Mussivand |
| 5,713,939 A | 2/1998 | Nedungadi et al. |
| 5,713,954 A | 2/1998 | Rosenberg et al. |
| 5,722,930 A | 3/1998 | Larson, Jr. et al. |
| 5,728,154 A | 3/1998 | Crossett et al. |
| 5,735,887 A | 4/1998 | Barreras, Sr. et al. |
| 5,741,314 A | 4/1998 | Daly et al. |
| 5,741,316 A | 4/1998 | Chen et al. |
| 5,749,909 A | 5/1998 | Schroeppel et al. |
| 5,751,125 A | 5/1998 | Weiss |
| 5,755,748 A | 5/1998 | Borza |
| 5,781,419 A | 7/1998 | Kutkut et al. |
| 5,945,762 A | 8/1999 | Chen et al. |
| 5,948,006 A | 9/1999 | Mann |
| 5,991,665 A | 11/1999 | Wang et al. |
| 5,995,874 A | 11/1999 | Borza |
| 6,047,214 A | 4/2000 | Mueller et al. |
| 6,058,330 A | 5/2000 | Borza |
| 6,067,474 A | 5/2000 | Schulman et al. |
| 6,076,016 A | 6/2000 | Feierbach |
| 6,088,619 A | 7/2000 | Hein et al. |
| 6,092,531 A | 7/2000 | Chen et al. |
| 6,112,121 A | 8/2000 | Paul et al. |
| 6,149,683 A | 11/2000 | Lancisi et al. |
| 6,212,430 B1 | 4/2001 | Kung |
| 6,233,485 B1 | 5/2001 | Armstrong et al. |
| 6,240,318 B1 | 5/2001 | Phillips |
| 6,254,525 B1 | 7/2001 | Reinhardt et al. |
| 6,263,247 B1 | 7/2001 | Mueller et al. |
| 6,275,737 B1 | 8/2001 | Mann |
| 6,324,430 B1 | 11/2001 | Zarinetchi et al. |
| 6,342,071 B1 | 1/2002 | Pless |
| 6,345,203 B1 | 2/2002 | Mueller et al. |
| 6,366,817 B1 | 4/2002 | Kung |
| 6,389,318 B1 | 5/2002 | Zarinetchi et al. |
| 6,400,991 B1 | 6/2002 | Kung |
| 6,424,867 B1 | 7/2002 | Snell |
| 6,430,444 B1 | 8/2002 | Borza |
| 6,434,194 B1 | 8/2002 | Eisenberg et al. |
| 6,442,434 B1 | 8/2002 | Zarinetchi et al. |
| 6,443,891 B1 | 9/2002 | Grevious |
| 6,451,055 B1 * | 9/2002 | Weiss .................. A61M 60/40 623/3.27 |
| 6,458,164 B1 | 10/2002 | Weiss |
| 6,478,820 B1 | 11/2002 | Weiss |
| 6,517,476 B1 | 2/2003 | Bedoya et al. |
| 6,579,315 B1 | 6/2003 | Weiss |
| 6,592,620 B1 | 7/2003 | Lancisi et al. |
| 6,641,612 B2 | 11/2003 | Pless |
| 6,648,914 B2 | 11/2003 | Berrang et al. |
| 6,671,554 B2 | 12/2003 | Gibson et al. |
| 6,810,289 B1 | 10/2004 | Shaquer |
| 6,831,944 B1 | 12/2004 | Misra et al. |
| 6,850,803 B1 | 2/2005 | Jimenez |
| 6,862,478 B1 | 3/2005 | Goldstein |
| 6,961,005 B2 | 11/2005 | Clement et al. |
| 6,978,181 B1 | 12/2005 | Snell |
| 7,003,353 B1 | 2/2006 | Parkhouse |
| 7,035,689 B1 | 4/2006 | Hawkins et al. |
| 7,062,331 B2 | 6/2006 | Zarinetchi et al. |
| 7,069,086 B2 | 6/2006 | Von Arx |
| 7,076,206 B2 | 7/2006 | Elferich et al. |
| 7,079,901 B1 | 7/2006 | Loftin et al. |

(56) References Cited

U.S. PATENT DOCUMENTS

| | | |
|---|---|---|
| 7,155,291 B2 | 12/2006 | Zarinetchi et al. |
| 7,173,411 B1 | 2/2007 | Pond |
| 7,191,007 B2 | 3/2007 | Desai et al. |
| 7,299,095 B1 | 11/2007 | Barlow et al. |
| 7,317,947 B2 | 1/2008 | Wahlstrand et al. |
| 7,512,443 B2 | 3/2009 | Phillips et al. |
| 7,515,967 B2 | 4/2009 | Phillips |
| 7,574,262 B2 | 8/2009 | Haugland et al. |
| 7,599,743 B2 | 10/2009 | Hassler, Jr. et al. |
| 7,672,732 B2 | 3/2010 | Sun et al. |
| 7,738,965 B2 | 6/2010 | Phillips et al. |
| 7,774,069 B2 | 8/2010 | Olson |
| 7,781,916 B2 | 8/2010 | Boys |
| 7,822,480 B2 | 10/2010 | Park et al. |
| 7,848,814 B2 | 12/2010 | Torgerson et al. |
| 7,962,211 B2 | 6/2011 | Torgerson et al. |
| 8,024,047 B2 | 9/2011 | Olson et al. |
| 8,027,735 B1 | 9/2011 | Tziviskos et al. |
| 8,032,486 B2 | 10/2011 | Townsend et al. |
| 8,050,068 B2 | 11/2011 | Hussmann et al. |
| 8,093,758 B2 | 1/2012 | Hussmann |
| 8,097,983 B2 | 1/2012 | Karalis et al. |
| 8,116,681 B2 | 2/2012 | Baarman |
| 8,126,563 B2 | 2/2012 | Ibrahim |
| 8,265,770 B2 | 9/2012 | Toy et al. |
| 8,311,638 B2 | 11/2012 | Aghassian |
| 8,428,712 B2 | 4/2013 | Davis et al. |
| 8,428,724 B2 | 4/2013 | Sage |
| 8,437,855 B2 | 5/2013 | Sjostedt et al. |
| 8,457,758 B2 | 6/2013 | Olson |
| 8,473,066 B2 | 6/2013 | Aghassian et al. |
| 8,515,112 B2 | 8/2013 | Crawford et al. |
| 8,543,209 B2 | 9/2013 | Tyers et al. |
| 8,626,308 B2 | 1/2014 | Meskens |
| 8,630,717 B2 | 1/2014 | Olson et al. |
| 8,676,337 B2 | 3/2014 | Kallmyer |
| 8,706,255 B2 | 4/2014 | Philips et al. |
| 8,738,148 B2 | 5/2014 | Olson et al. |
| 8,764,621 B2 | 6/2014 | Badstibner et al. |
| 8,766,788 B2 | 7/2014 | D'Ambrosio |
| 8,903,515 B2 | 12/2014 | Mashiach |
| 8,972,012 B2 | 3/2015 | Lim |
| 9,192,772 B1 | 11/2015 | Kishiyama et al. |
| 9,603,984 B2 | 3/2017 | Romero et al. |
| 9,855,376 B2 | 1/2018 | Bluvshtein et al. |
| 10,149,933 B2 | 12/2018 | Bluvshtein et al. |
| 10,193,395 B2 | 1/2019 | Bluvshtein et al. |
| 10,342,908 B2 | 7/2019 | Bluvshtein et al. |
| 10,376,625 B2 | 8/2019 | Bluvshtein et al. |
| 10,406,267 B2 | 9/2019 | Lucke et al. |
| 2002/0021226 A1 | 2/2002 | Clement et al. |
| 2002/0032471 A1 | 3/2002 | Loftin et al. |
| 2002/0087204 A1 | 7/2002 | Kung et al. |
| 2002/0128709 A1 | 9/2002 | Pless |
| 2002/0177884 A1 | 11/2002 | Ahn et al. |
| 2003/0045912 A1 | 3/2003 | Williams et al. |
| 2003/0085684 A1 | 5/2003 | Tsukamoto et al. |
| 2003/0171792 A1 | 9/2003 | Zarinetchi et al. |
| 2004/0034393 A1 | 2/2004 | Hansen et al. |
| 2004/0039423 A1 | 2/2004 | Dolgin |
| 2004/0049245 A1 | 3/2004 | Gass et al. |
| 2005/0065570 A1 | 3/2005 | Stein et al. |
| 2005/0075694 A1 | 4/2005 | Schmeling et al. |
| 2005/0075696 A1 | 4/2005 | Forsberg et al. |
| 2005/0131491 A1 | 6/2005 | Shaquer |
| 2005/0245996 A1 | 11/2005 | Phillips et al. |
| 2005/0288739 A1 | 12/2005 | Hassler, Jr. et al. |
| 2005/0288741 A1 | 12/2005 | Hassler, Jr. et al. |
| 2006/0020305 A1 | 1/2006 | Desai et al. |
| 2006/0036127 A1 | 2/2006 | Delgado, III |
| 2006/0167333 A1 | 7/2006 | Moore et al. |
| 2006/0184204 A1 | 8/2006 | He |
| 2006/0247737 A1 | 11/2006 | Olson |
| 2006/0267790 A1 | 11/2006 | Matthiessen et al. |
| 2007/0060787 A1 | 3/2007 | Peters et al. |
| 2007/0255349 A1 | 11/2007 | Torgerson et al. |
| 2007/0255350 A1 | 11/2007 | Torgerson et al. |
| 2008/0065173 A1 | 3/2008 | Wahlstrand et al. |
| 2008/0198947 A1 | 8/2008 | Zierhofer |
| 2008/0255631 A1 | 10/2008 | Sjostedt et al. |
| 2008/0303480 A1 | 12/2008 | Prutchi et al. |
| 2009/0067653 A1 | 3/2009 | Meskens et al. |
| 2009/0281597 A1 | 11/2009 | Parramon et al. |
| 2010/0010582 A1 | 1/2010 | Carbunaru et al. |
| 2010/0033023 A1 | 2/2010 | Baarman |
| 2010/0033240 A1 | 2/2010 | Denison et al. |
| 2010/0063347 A1 | 3/2010 | Yomtov et al. |
| 2010/0164296 A1 | 7/2010 | Kurs et al. |
| 2010/0249886 A1 | 9/2010 | Park et al. |
| 2010/0268305 A1 | 10/2010 | Olson |
| 2010/0292759 A1 | 11/2010 | Hahn |
| 2010/0327887 A1 | 12/2010 | Denison et al. |
| 2011/0004278 A1 | 1/2011 | Aghassian et al. |
| 2011/0093048 A1 | 4/2011 | Aghassian |
| 2011/0101790 A1 | 5/2011 | Budgett |
| 2011/0106210 A1 | 5/2011 | Meskens |
| 2011/0301669 A1 | 12/2011 | Olson |
| 2011/0313490 A1 | 12/2011 | Parramon et al. |
| 2012/0032522 A1 | 2/2012 | Schatz et al. |
| 2012/0095528 A1 | 4/2012 | Miller, III et al. |
| 2012/0154143 A1 | 6/2012 | D'Ambrosio |
| 2012/0157753 A1 | 6/2012 | D'Ambrosio |
| 2012/0157754 A1 | 6/2012 | D'Ambrosio |
| 2012/0197352 A1 | 8/2012 | Carbunaru et al. |
| 2012/0215285 A1 | 8/2012 | Tahmasian |
| 2012/0265003 A1 | 10/2012 | D'Ambrosio et al. |
| 2013/0023958 A1 | 1/2013 | Fell |
| 2013/0041429 A1 | 2/2013 | Aghassian |
| 2013/0043736 A1 | 2/2013 | Zilbershlag |
| 2013/0046361 A1 | 2/2013 | DiGiore et al. |
| 2013/0123881 A1 | 5/2013 | Aghassian |
| 2013/0127253 A1 | 5/2013 | Stark |
| 2013/0158631 A1 | 6/2013 | Shea et al. |
| 2013/0163688 A1 | 6/2013 | Calvin |
| 2013/0278226 A1 | 10/2013 | Cong et al. |
| 2013/0310629 A1 | 11/2013 | Lafontaine |
| 2013/0317345 A1 | 11/2013 | Frustaci et al. |
| 2013/0331638 A1 | 12/2013 | Cameron et al. |
| 2013/0338734 A1 | 12/2013 | Hoyer et al. |
| 2014/0005749 A1 | 1/2014 | Stahmann et al. |
| 2014/0031607 A1 | 1/2014 | Zilbershlag et al. |
| 2014/0139034 A1 | 5/2014 | Sankar et al. |
| 2014/0243944 A1 | 8/2014 | Stevenson et al. |
| 2014/0371823 A1 | 12/2014 | Mashiach et al. |
| 2015/0069847 A1 | 3/2015 | Meyer et al. |
| 2015/0073203 A1 | 3/2015 | Wariar et al. |
| 2015/0207331 A1 | 7/2015 | Petersen |
| 2015/0209591 A1 | 7/2015 | Meskens |
| 2015/0333801 A1 | 11/2015 | Hosotani |
| 2015/0364861 A1 | 12/2015 | Lucke et al. |
| 2015/0380988 A1 | 12/2015 | Chappell et al. |
| 2016/0175600 A1 | 6/2016 | Amir et al. |
| 2016/0197511 A1 | 7/2016 | Atasoy et al. |
| 2016/0206799 A1 | 7/2016 | Lucke et al. |
| 2016/0248265 A1 | 8/2016 | Oo et al. |
| 2016/0294225 A1 | 10/2016 | Blum et al. |
| 2016/0303301 A1 | 10/2016 | Bluvshtein et al. |
| 2017/0119947 A1 | 5/2017 | Eldridge et al. |
| 2018/0207338 A1 | 7/2018 | Bluvshtein et al. |
| 2019/0111198 A1 | 4/2019 | Bluvshtein et al. |
| 2019/0157913 A1 | 5/2019 | Bluvshtein et al. |

FOREIGN PATENT DOCUMENTS

| | | |
|---|---|---|
| FR | 2587221 | 3/1987 |
| JP | 2597623 B2 | 4/1997 |
| WO | 8301006 | 3/1983 |
| WO | 8700420 | 1/1987 |
| WO | 9809588 | 3/1998 |
| WO | 200191678 A1 | 12/2001 |
| WO | 2007126454 A2 | 11/2007 |
| WO | 2008106717 A1 | 9/2008 |
| WO | 2009029977 A1 | 3/2009 |
| WO | 2010042057 A1 | 4/2010 |

(56) References Cited

FOREIGN PATENT DOCUMENTS

| WO | 2010133702 | A2 | 11/2010 |
|---|---|---|---|
| WO | 2011119352 | A1 | 9/2011 |
| WO | 2012077088 | A2 | 6/2012 |
| WO | 2012077088 | A3 | 6/2012 |
| WO | 2014036449 | A1 | 3/2014 |
| WO | 2014169940 | A1 | 10/2014 |

OTHER PUBLICATIONS

Andia, et al., "Closed Loop Wireless Power Transmission for Implantable Medical Devices," IEEE, 2011, pp. 404-407.

Bonsor, "How Artificial Hearts Work," HowStuffWorks, Aug. 9, 2001, downloaded from HowStuffWorks.com. at http://science.howstuffworks.com/innovation/everyday-innovations/artificial-heart.htm (12 pages).

German Patent & Trademark Office, "First Office Action", Application No. 102016106683.4, dated Mar. 5, 2018, 17 pages.

Knecht, et al., "Optimization of Transcutaneous Energy Transfer Coils for High Power Medical Applications," Workshop on Control and Modeling for Power Electronics (COMPEL), 2014, pp. 1-10.

Ng, et al., "Closed-Loop Inductive Link for Wireless Powering of a High Density Electrode Array Retinal Prosthesis," IEEE, 2009, pp. 92-97.

Ng, et al., "Wireless Power Delivery for Retinal Prostheses," 33rd Annual International Conference of the IEEE EMBS, Aug. 30, 2011-Sep. 3, 2011, pp. 8356-8360.

Shmilovitz, et al., "Noninvasive Control of the Power Transferred to an Implanted Device by an Ultrasonic Transcutaneous Energy Transfer Link," IEEE Transactions on Biomedical Engineering, Apr. 2014, pp. 995-1004, vol. 61, No. 4.

Mirbozorgi, et al., "A Transcutaneous Power Transfer Interface Based on a Multicoil Inductive Link", Aug. 28-Sep. 1, 2012, pp. 1659-1662, 34th Annual International Conference of the IEEE EMBS, San Diego, CA.

Ng, et al., "Wireless Power Delivery for Retinal Prostheses", 33rd Annual International Conference of the IEEE EMBS, pp. 8356-8360, Aug. 30-Sep. 3, 2011, Boston MA.

\* cited by examiner

DATA COMMUNICATION IN A TRANSCUTANEOUS ENERGY TRANSFER SYSTEM

CROSS-REFERENCE TO RELATED APPLICATION

This application is a division of U.S. application Ser. No. 14/995,962, filed Jan. 14, 2016, now U.S. Pat. No. 10,406,267, which claims the benefit of U.S. Provisional Application No. 62/104,451, filed Jan. 16, 2015. The entirety of each are herein incorporated by reference

STATEMENT REGARDING FEDERALLY SPONSORED RESEARCH OR DEVELOPMENT

This invention was made with Government support under one or more Small Business Innovation Research (SBIR) grants awarded by the Public Health Service (PHS). The Government has certain rights in the invention.

TECHNICAL FIELD

The technology described herein relates to systems and methods for data communication in a transcutaneous energy transfer system.

BACKGROUND

Currently, there is a need to deliver electric power to implanted medical devices such as artificial hearts and ventricle assist devices. It is possible to deliver power non-invasively through electromagnetic energy transmitted through the skin. In connection with systems that deliver energy in this manner, it is possible to establish data communication links between external and implanted components. Typically, these systems use an external RF link (Bluetooth, MILS, other proprietary protocols) for communicating data and for regulation of the power channel between external and implanted components. With this approach, the safety of the patient and reliability of the system depends on the health of that RF link. For example, if the system relies on an external RF link for output voltage regulation then even a short lived RF communication dropout will result in overvoltage of the system output voltage, which, in turn, could damage upstream electronics. Thus, there is a need for improved communication methods in systems that deliver electromagnetic energy transmitted through the skin of subject or patient that has an implanted medical device.

SUMMARY

Embodiments of the present invention are directed to the use of an inductive link for a communication channel in a transcutaneous energy transfer system. An attribute of the inductive link or of a signal transmitted over the inductive link is modulated to encode a data signal. Attributes of the power signal that may be modulated include the amplitude, the frequency, and/or the phase. The system may be configured to transfer data from the external primary to the implanted secondary, from the implanted secondary to the external primary, or both.

In one aspect, a method of communicating data in a transcutaneous energy transmission device is disclosed, the method including transferring electrical power from an external primary to an implanted secondary by driving the external primary with a first time-varying electrical signal such that a second time-varying electrical signal is induced in the implanted secondary; encoding the first time-varying signal with a data signal by modulating an attribute of the first time-varying electrical signal as electrical power is transferred from the external primary to the implanted secondary; and receiving the data signal at the implanted secondary by demodulating the secondary time-varying electrical signal as electrical power is transferred from the external primary to the implanted secondary.

In some implementations, encoding the first time-varying signal with a data signal includes modulating the amplitude of the first time-varying electrical signal. In some implementations, the amplitude of the first time-varying electrical signal is modulated using a transformer connected to the drain of a power transistor used to transfer power from the primary to the secondary. In some implementations, the amplitude of the first time-varying electrical signal is indirectly modulated by shifting the first time-varying electrical signal among different subharmonic frequencies. In some implementations, the amplitude of the first time-varying electrical signal is modulated by modulating an output of a signal driver that is connected to the gate of a power transistor used to transfer power from the primary to the secondary.

Some implementations include alternating the electrical power transfer between a power supply mode and an idle mode responsive to power consumption in the implanted secondary; wherein the operation of encoding the first time-varying signal with a data signal by modulating the amplitude of the first time-varying electrical signal occurs during the power supply mode. Some implementations include alternating the electrical power transfer between a power supply mode and an idle mode responsive to power consumption in the implanted secondary; wherein the operation of encoding the first time-varying signal with a data signal by modulating the amplitude of the first time-varying electrical signal occurs during the idle mode.

Some implementations include encoding the first time-varying signal with a data signal includes modulating the frequency of the first time-varying electrical signal. In some implementations, the frequency of the first time-varying electrical signal is directly modulated by shifting the first time-varying electrical signal within a range of drive frequencies.

Some implementations include alternating the electrical power transfer between a power supply mode and an idle mode responsive to power consumption in the implanted secondary; wherein the operation of encoding the first time-varying signal with a data signal by modulating the frequency of the first time-varying electrical signal occurs during the power supply mode. Some implementations include alternating the electrical power transfer between a power supply mode and an idle mode responsive to power consumption in the implanted secondary; wherein the operation of encoding the first time-varying signal with a data signal by modulating the frequency of the first time-varying electrical signal occurs during the idle mode.

Some implementations include encoding the first time-varying signal with a data signal includes modulating the phase of the first time-varying electrical signal. Some implementations include alternating the electrical power transfer between a power supply mode and a lower power mode responsive to power consumption in the implanted secondary; wherein the operation of encoding the first time-varying signal with a data signal by modulating the phase of the first time-varying electrical signal occurs during the power supply mode.

In some implementations, the data signal is a first data signal, the method further including encoding the second time-varying signal with a second data signal by modulating an attribute of the second time-varying electrical signal as electrical power is transferred from the external primary to the implanted secondary; and receiving the second data signal at the external primary by demodulating the first time-varying electrical signal as electrical power is transferred from the external primary to the implanted secondary.

Some implementations include time multiplexing the first and second data signals. In some implementations, encoding the first time-varying signal with the first data signal includes modulating the amplitude of the first time-varying electrical signal at a first amplitude level; encoding the second time-varying signal with the second data signal includes modulating the amplitude of the second time-varying electrical signal at a second amplitude level that is different from the first amplitude level; and the first and second time varying signals are modulated at the same time.

In some implementations, encoding the first time-varying signal with the first data signal includes modulating the frequency of the first time-varying electrical signal; encoding the second time-varying signal with the second data signal includes modulating the amplitude of the second time-varying electrical signal; and the first and second time varying signals are modulated at the same time. In some implementations, encoding the first time-varying signal with the first data signal includes modulating the phase of the first time-varying electrical signal; encoding the second time-varying signal with the second data signal includes modulating the amplitude of the second time-varying electrical signal; and the first and second time varying signals are modulated at the same time.

Some implementations include alternating the electrical power transfer between a power supply mode and an idle mode responsive to power consumption in the implanted secondary; wherein the operation of encoding the second time-varying signal with the second data signal by modulating an attribute of the second time-varying electrical signal occurs during the idle mode. In some implementations, the second time-varying electrical signal is modulated by a resistive loading of a circuit that includes a resonant tank associated with the secondary; and the first time-varying electrical signal is demodulated in the primary by sensing changes that occur in a primary current due to the resistive loading in the secondary. In some implementations, the second time-varying electrical signal is modulated by a reactive loading of a circuit that includes a resonant tank associated with the secondary; and the first time-varying electrical signal is demodulated in the primary by sensing changes that occur in the primary current due to the reactive loading in the secondary.

In another aspect, a method of communicating data in a transcutaneous energy transmission device is disclosed, the method including transferring electrical power from an external primary to an implanted secondary by driving the external primary with a first time-varying electrical signal such that a second time-varying electrical signal is induced in the implanted secondary; alternating the electrical power transfer between a power supply mode and an idle mode responsive to power consumption in the implanted secondary; encoding the secondary time-varying signal with a data signal by modulating an attribute of the second time-varying electrical signal as electrical power is transferred from the external primary to the implanted secondary; and receiving the data signal at the external primary by demodulating the first time-varying electrical signal as electrical power is transferred from the external primary to the implanted secondary; wherein the operation of encoding the second time-varying signal with the second data signal by modulating an attribute of the second time-varying electrical signal occurs during the idle mode.

In some implementations, the second time-varying electrical signal is modulated by a resistive loading of a circuit that includes a resonant tank associated with the secondary; and the first time-varying electrical signal is demodulated in the primary by sensing changes that occur in a primary current due to the resistive loading in the secondary. In some implementations, the second time-varying electrical signal is modulated by a reactive loading of a circuit that includes a resonant tank associated with the secondary; and the first time-varying electrical signal is demodulated in the primary by sensing changes that occur in the primary current due to the reactive loading in the secondary.

In another aspect, a system for communicating data in an transcutaneous energy transfer system is disclosed, the system including a resonant circuit associated with an external primary; a power transistor connected to the resonant circuit and configured to drive the resonant circuit with a first time-varying electrical signal; a power driver connected to the power transistor and configured to set the frequency of the time-varying electrical signal to a resonant frequency to enable power transfer from the external primary to an implanted secondary; and a communication driver operatively connected to the power transistor and configured to encode the first time-varying electrical signal with a data signal by modulating an attribute of the time-varying electrical signal as electrical power is transferred from the external primary to the implanted secondary.

In some implementations, the first time-varying electrical signal induces a second time-varying electrical signal in the implanted secondary; and the implanted secondary includes a communication receiver configured to receive the data signal by demodulating the secondary time-varying electrical signal as electrical power is transferred from the external primary to the implanted secondary. Some implementations include a transformer having a primary side connected to the communication driver and a secondary that connects the DC power source to the high side of the power transistor; wherein the communication driver directly modulates first time-varying electrical signal through the transformer. Some implementations include a regulator connecting a DC power source to the high side of the power transistor wherein the regulator is controlled by the communication driver; wherein the communication driver directly modulates first time-varying electrical signal through the transformer.

In some implementations, the communication driver indirectly modulates the first time-varying electrical signal amplitude by adjusting frequency of the output of the power driver to a subharmonic of the fundamental driver frequency. In some implementations, the communication driver encodes the first time-varying signal with the data signal by modulating the frequency of the first time-varying electrical signal. In some implementations, the communication driver encodes the first time-varying signal with the data signal by modulating the phase of the first time-varying electrical signal.

In some implementations, the power driver alternates the electrical power transfer between a power supply mode and an idle mode responsive to power consumption in the implanted secondary; and the communication driver encodes the first time-varying signal with the data signal by modulating the attribute of the first time-varying electrical signal during the power supply mode. Some implementations include the power driver alternates the electrical power transfer between a power supply mode and an idle mode responsive to power consumption in the implanted secondary; and the communication driver encodes the first time-varying signal with the data signal by modulating the attribute of the first time-varying electrical signal during the idle mode.

In another aspect, a method of communicating data in a transcutaneous energy transmission device is disclosed, the method including transferring electrical power from an external primary to an implanted secondary by driving the external primary with a first time-varying electrical signal such that a second time-varying electrical signal is induced in the implanted secondary; alternating the electrical power transfer between a power supply mode and an idle mode responsive to power consumption in the implanted secondary; encoding the secondary time-varying signal with a data signal by modulating an attribute of the second time-varying electrical signal as electrical power is transferred from the external primary to the implanted secondary; and receiving the data signal at the external primary by demodulating the first time-varying electrical signal as electrical power is transferred from the external primary to the implanted secondary; wherein the operation of encoding the second time-varying signal with the second data signal by modulating an attribute of the second time-varying electrical signal occurs during the power supply mode.

In some implementations, the second time-varying electrical signal is modulated by a resistive loading of a circuit that includes a resonant tank associated with the secondary; and the first time-varying electrical signal is demodulated in the primary by sensing changes that occur in a primary current due to the resistive loading in the secondary.

In some implementations, the second time-varying electrical signal is modulated by a reactive loading of a circuit that includes a resonant tank associated with the secondary; and the first time-varying electrical signal is demodulated in the primary by sensing changes that occur in a primary current due to the reactive loading in the secondary.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

DETAILED DESCRIPTION

Embodiments of the present invention are directed to the use of an inductive link for a communication channel in a transcutaneous energy transfer system. An attribute of the inductive link or of a signal transmitted over the inductive link is modulated to encode a data signal. Attributes of the power signal that may be modulated include the amplitude, the frequency, and/or the phase. The system may be configured to transfer data from the external primary to the implanted secondary, from the implanted secondary to the external primary, or both.

System Overview

Figure 1:
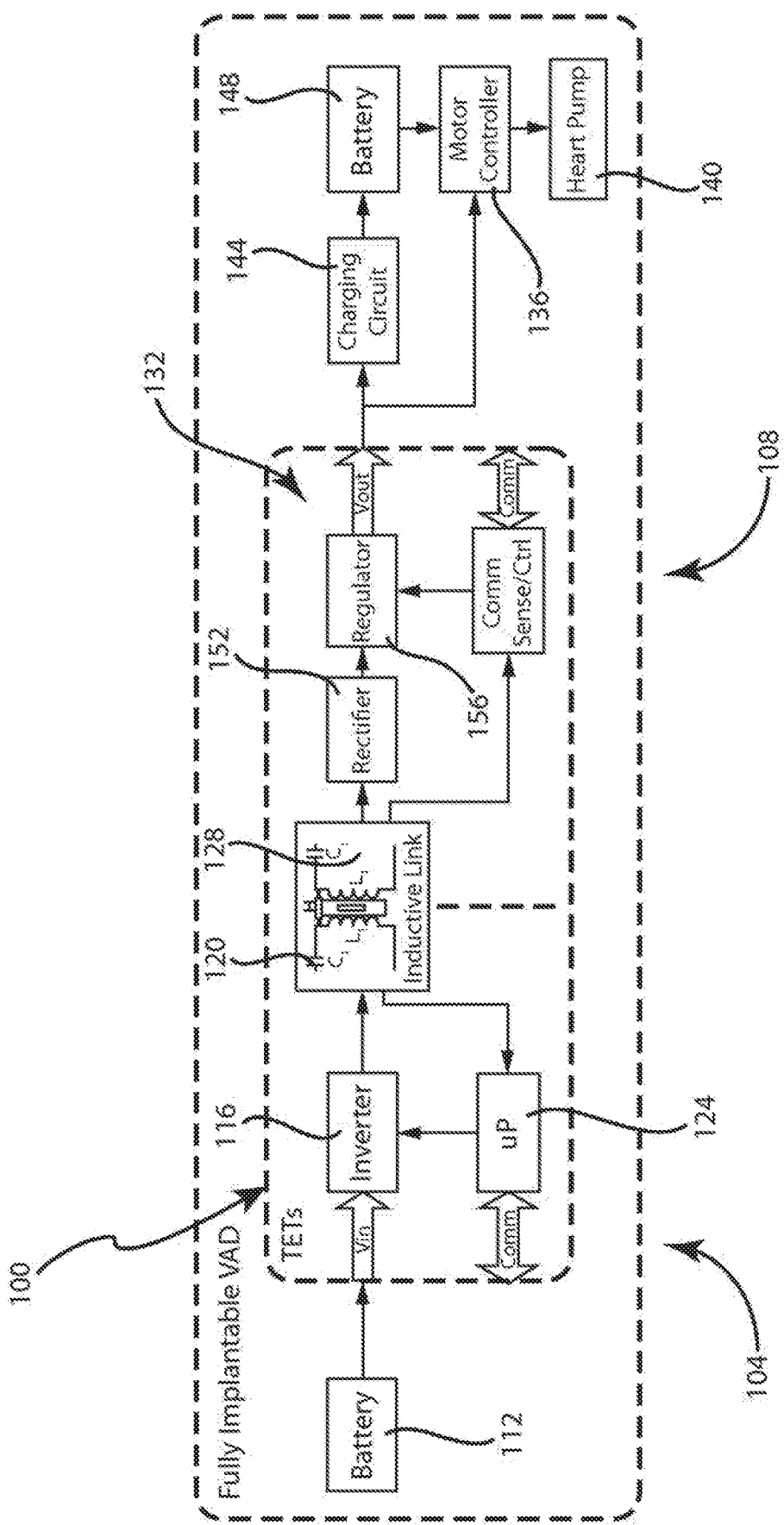
FIG. 1 is a block diagram of a wireless power transfer system in accordance with embodiments discussed herein.

FIG. 1 is a block diagram of a wireless power transfer system 100 in accordance with embodiments discussed herein. The system 100 may be referred to as a transcutaneous energy transfer system (TETS) when applied to implantable electronic applications. The system 100 has an external assembly 104 that is provided at an external location outside of a subject and an internal assembly 108 that is implanted within the subject. The internal assembly includes an implantable medical device. The implantable medical device may be any medical device capable of being implanted in a subject, such as a heart pump, an artificial heart, a right ventricle assist device, a left ventricle assist device, a BIVAD, a minimally invasive circulatory support system, a cardiac pace maker, and so on. While the implanted device may be any implantable medical device, this disclosure describes the transcutaneous energy transfer system 100 in the context of a heart pump 140 by way of example and not limitation.

Figure 2:
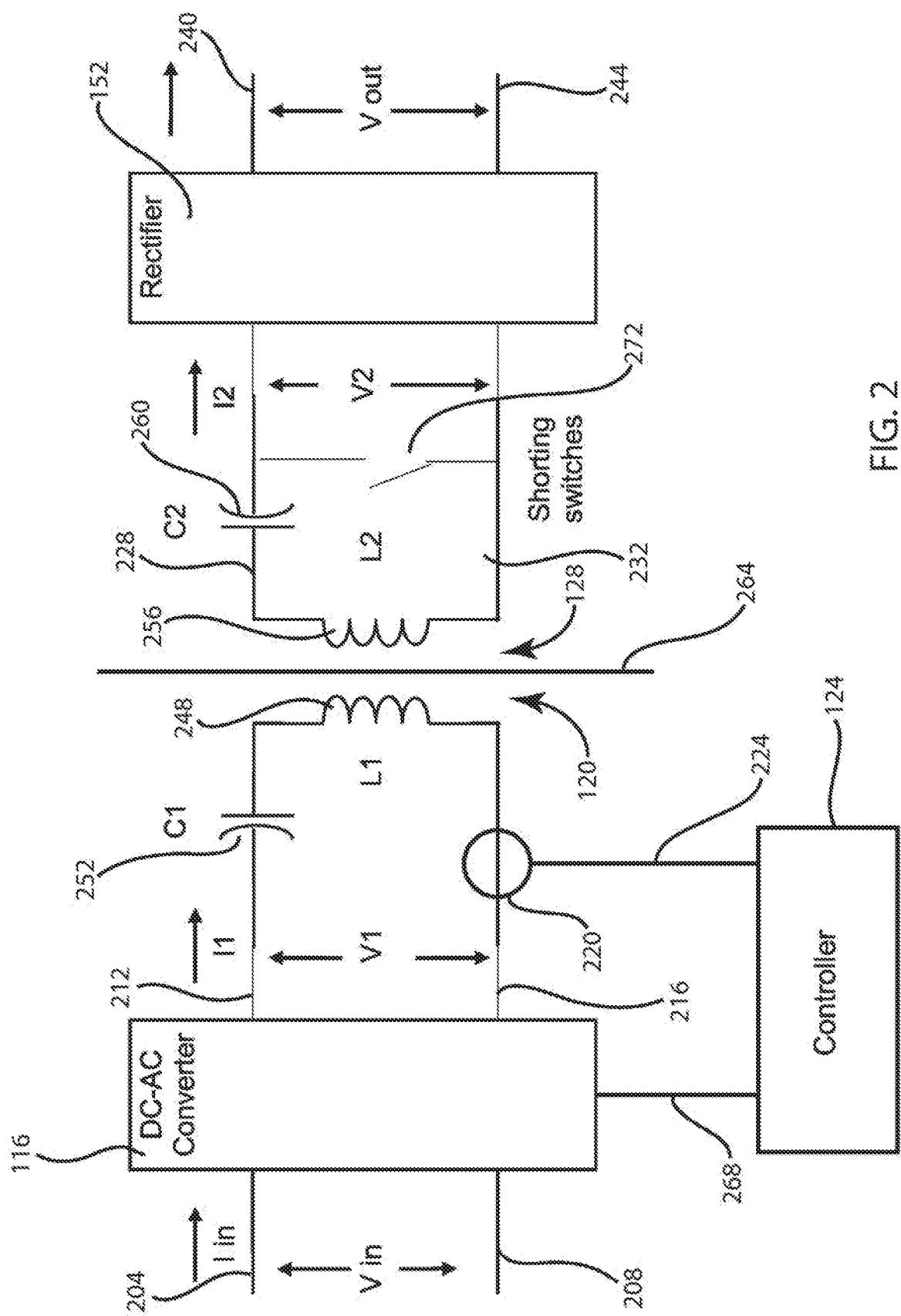
FIG. 2 is circuit diagram for certain components of the system shown in FIG. 1.

As shown in FIG. 1, the external assembly 104 may include an external resonant network 120. Similarly, the internal assembly 108 may include an internal resonant network 128. The external assembly 104 and the internal assembly 108 are also shown in FIG. 2, which is a circuit diagram that includes certain components of the transcutaneous energy transfer system 100. As shown in FIG. 2, the external resonant network 120 may include an external coupler in the form of an inductive coil 248 and a capacitor 252 connected in series. Similarly, the internal resonant network 128 may include an internal coupler in the form of an inductive coil 256 and a capacitor 260 connected in series. It should be appreciated that the series-series topology illustrated in FIG. 2 is shown by way of example and not limitation. Alternative embodiments may be used that employ different circuit topologies, such as series-parallel, parallel-series, parallel-parallel and so on.

Figure 3A:
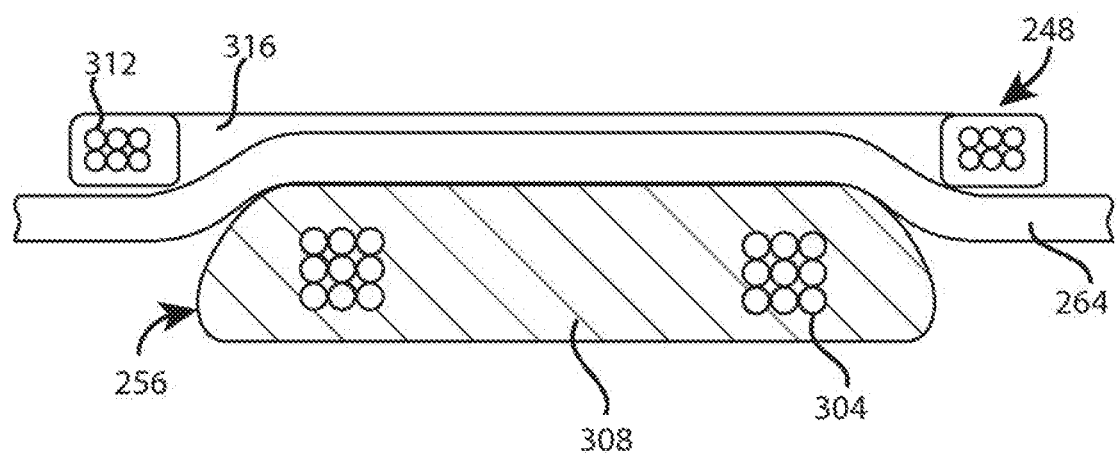
FIGS. 3A and 3B are schematic illustrations of the internal and external coils shown in FIG. 1.
Figure 3B:
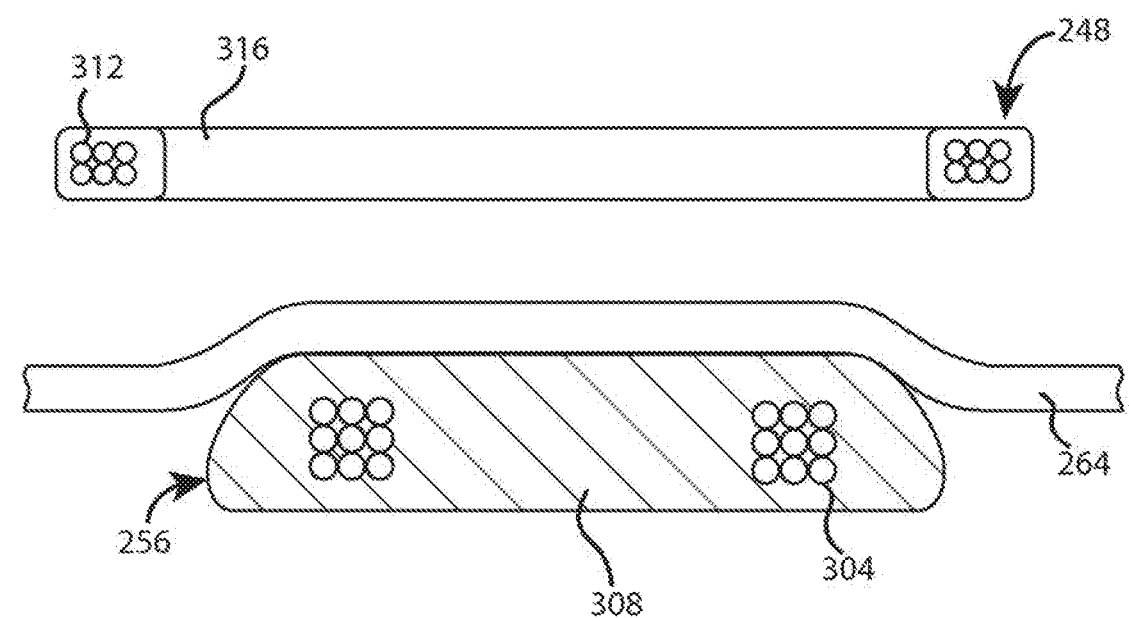

FIGS. 3A and 3B are schematic illustrations of the internal 256 and external 248 coils. In FIG. 3A, the internal coil 256 is disposed beneath the skin 264 of a subject, and the external coil 248 is disposed generally adjacent the internal coil 256. In FIG. 3B, the internal coil 256 is disposed beneath the skin 264 of a subject, and the external coil 248 is disposed at some distance from the internal coil 256. As shown in FIGS. 3A and 3B, the internal coil 256 may have a plurality of conductive windings 304 disposed in a circular insulating member 308. Similarly, the external coil 248 may have a plurality of conductive windings 312 disposed in an insulating ring 316. The inductance of each of the coils 256, 248 may be determined by the number, diameter and spacing of the windings 304, 312. The inductive or electromagnetic coupling between the coils 248, 256 is a function of their physical proximity, operating frequencies, coil sizes, and inductances. While the coils shown in FIGS. 3A and 3B have a generally circular shape, other shapes and structures may be used to implement the internal 256 and external 248 coils, depending on the implementation. For example, the coils 248, 256 may be shaped as a triangle, square, rectangle, pentagon, octagon, and so on. Generally, the coils 248, 256 may be shaped as polygons of any number of sides, which may be equal or unequal in length. The coils may be straight in certain portions and/or curved in certain portions. The coils 248, 256 may be arranged in a planar configuration. Alternatively, the coils 248, 256 may be arranged such that portions of the coils lie in different planes.

The coils 248, 256 together constitute a loosely coupled transformer, with the external coil 248 acting as a primary winding and the internal coil 256 acting as a secondary winding. The coils 248, 256 and the capacitors 252, 260 with which they may be connected may form a resonant circuit. The coils 248, 256 may be tuned to the same or different resonant frequencies. For example, the coils 248, 256 may be series tuned to a power transmission frequency of about 200 kHz. The external coil 248 may induce an electric current in the internal coil 256, which current generally behaves in accordance with the following equation:

$$\frac{V_2}{I_2} = \frac{V_2}{I_2} = \omega \cdot k \cdot \sqrt{L_1 \cdot L_2} \quad (1)$$

In Equation (1), Ii is the current induced in the external resonant network 120. I2 is the current induced in the internal coil network 128. V1 is the voltage across the external resonant network 120. V2 is the voltage across the internal resonant network 128. w is the frequency of the voltage across the coils 248, 256, where the coil networks are tuned to the same frequency w. Li is the inductance of the external coil 248. L2 is the inductance of the internal coil 256. k is the coupling coefficient.

Referring to both FIG. 1 and FIG. 2, the external assembly 104 includes a power supply 112, which generally provides power in the form of a DC voltage. In some embodiments, the power supply 112 is a portable battery or battery pack providing a DC voltage of between 10 and 18 volts. The external assembly 104 also includes an inverter 116 connected to the power supply 112 via a pair of conductive lines 204, 208. The power supply 112 supplies the DC voltage to the inverter 116, which converts the DC voltage into a high-frequency voltage. The high-frequency voltage is provided to the external resonant network 120 via a pair of conductors 212, 216. A current sensor 220 may be used to sense the electric current flowing within the conductor 216. The current sensor 220 may be configured to sense either or both of the magnitude and phase of the electric current in the conductor 216. A controller 124 connected to the current sensor 220 via a conductor 224 may be used to control the operation of the inverter 116, based on one or more characteristics of the current sensed by the sensor 220. The controller 124 may also be configured to control the voltage Vin, that is provided by the power supply 112. The external coil network 120, which is disposed adjacent the skin 264 of the subject, transfers electric power through the skin 264 of the subject to the internal coil network 128 disposed beneath the skin 264 of the subject.

The internal assembly 108 is disposed beneath the skin 264 of the subject and includes the internal coil network 128. The internal coil network 128 is connected to a power circuit 132 via a pair of conductors 228, 232. The power circuit 132 includes a rectifier 152 that performs full wave rectification of the sinusoidal AC current induced in the internal coil 256 by the external coil 248.

In one embodiment, the rectifier 152 includes four switching elements, which may be provided in the form of diodes or Schottky diodes. During a first half of the AC power cycle, a first pair of diodes provides a conductive path up from ground, through the internal coil 256, and out to conductor line 228. During a second half of the AC power cycle, a second pair of diodes provides a conductive path up from ground, through the internal coil 256, and out to conductor line 228. In this way, the rectifier 152 converts AC power provided by the internal coil network 128 into DC power that can be used by various components of the internal assembly 108.

The power circuit 132 additionally includes a regulator 156 that regulates power supplied by the rectifier 152. The regulator 156 supplies electric power to a controller 136 and other elements via a pair of conductors 240, 244. The controller 136 may control the operation of the heart pump 140. The power conductors 240, 244 also supply electric power to the heart pump 140 through the controller 136. The regulator 156 may be a shunt type regulator that repeatedly charges and discharges a power supply capacitor. In other implementations, other types of regulators, such as a series regulator, may be used. In one embodiment, the power supply capacitor is a component of the charging circuit 144. The voltage across the power capacitor is output via the lines 240, 244 to the controller 136 and to the implanted medical device such as heart pump 140.

During operation, the motor controller 136 drives the heart pump 140 to pump blood through the artificial heart assembly, drawing electric current from the power supply capacitor associated with the charging circuit 144. As current is drawn from the capacitor, the voltage across the capacitor decreases. To replenish the voltage on the capacitor, the power circuit 132 periodically operates in a power supply mode in which electric current generated by the rectifier 152 is provided to the capacitor via the lines 240, 244. When not operating in the power supply mode, the power circuit 132 operates in an idle mode in which current is not supplied to the capacitor.

In the case of shunt type regulator 156 shorting of the resonant secondary 128 may be accomplished by one or more shorting switches 272 that operate to shift the power circuit 132 between the power supply mode and the idle mode. In the power supply mode, the shorting switches 272 open to allow current to flow from the internal resonant network 128, through the rectifier 152, and out to the conductor line 240/244. In idle mode, the shorting switches 272 close to short internal resonant network 128 so that current flows only within resonant network 228 rather than out to the conductor lines 240/244.

The magnitude of the output voltage across the power supply capacitor associated with regulator circuit 156 may control whether the shorting switches 272 are open or closed and thus whether the power circuit 132 operates in the power supply mode or in the idle mode. For example, if the output voltage falls below a certain value, the shorting switches 272 open and the power circuit 132 operates in the power supply mode. When the output voltage rises to a certain value, the shorting switches 272 close and the power supply circuit 132 operates in the idle mode. By selectively supplying current to the power supply capacitor only during certain times (i.e. the power supply mode), the voltage across the capacitor is regulated, or maintained within a predetermined voltage range, such as between about 13 and about 14 volts, for example.

In one embodiment, the shorting switches 272 are implemented as a pair of switching transistors, such as field-effect transistors, though any suitable structure may be used. For example, the shorting switches 272 may be implemented using bipolar junction transistors, and so on. The switching transistors may be configured to short diodes associated with the rectifier 152 in a conductive state and to not do so in a non-conductive state. A switching control circuit may control the conductive state of the switching transistors based on the output voltage across the power supply capacitor associated with the regulator circuit 156. When the output voltage is above a certain value, the control circuit turns on the switching transistors to short diodes associated with the rectifier 152. Here, current flows through the internal resonant network 128 and through the conductive transistors. When the output voltage is below a certain value, the control circuit turns off the switching transistors so that the diodes associated with the rectifier 152 are not shorted. Here, current is allowed to flow from the internal resonant network 128, through the rectifier 152, and out to the conductor line 240/244.

The external assembly 104 may be responsive to the internal assembly shifting between the power supply mode and the idle mode. As mentioned above, the external assembly includes a controller 124 that may be used to control the operation of the inverter 116 based on one or more characteristics of the current sensed by the sensor 220. In this regard, the controller 124 may change the frequency at which the inverter 116 operates to conserve electric power during the idle mode. During the idle mode, when electric current is not being supplied to the capacitor associated with the charging circuit 144, the power transmitted to the internal coil 256 by the external coil 248 is reduced in order to conserve the power of the power supply 112. This is accomplished by changing the frequency at which the inverter 116 operates.

As noted above, the internal and external coils 248, 256 may be tuned to a power transmission frequency, such as about 200 kHz. Consequently, when it is desired to transmit power to the internal coil 256, the inverter 116 is operated at the power transmission frequency to which it is tuned. However, when it is not necessary to transmit a significant amount of power, such as during the idle mode above, the frequency of the inverter 116 is changed. The frequency at which the inverter 116 operates during the power-supply mode may be changed to an odd sub-harmonic of that frequency during the idle mode. For example, the idle mode frequency may be ⅓, ⅕, ⅐, ⅑ of the power supply mode frequency. The amount of power transmitted to the internal coil 256 varies with the idle mode frequency, with less power being transmitted at the seventh subharmonic (i.e. ⅐ of the power supply mode frequency, or 28.6 kHz if the power transmission frequency is 200 kHz) than at the third subharmonic (i.e. ⅓ of the power supply mode frequency). Since odd subharmonics of a fundamental frequency still contain, in accordance with Fourier analysis, some components of the fundamental frequency, using an odd subharmonic of the power supply mode frequency during idle mode will still result in some power being transmitted to the internal coil 256, which is generally desirable.

Figure 4:
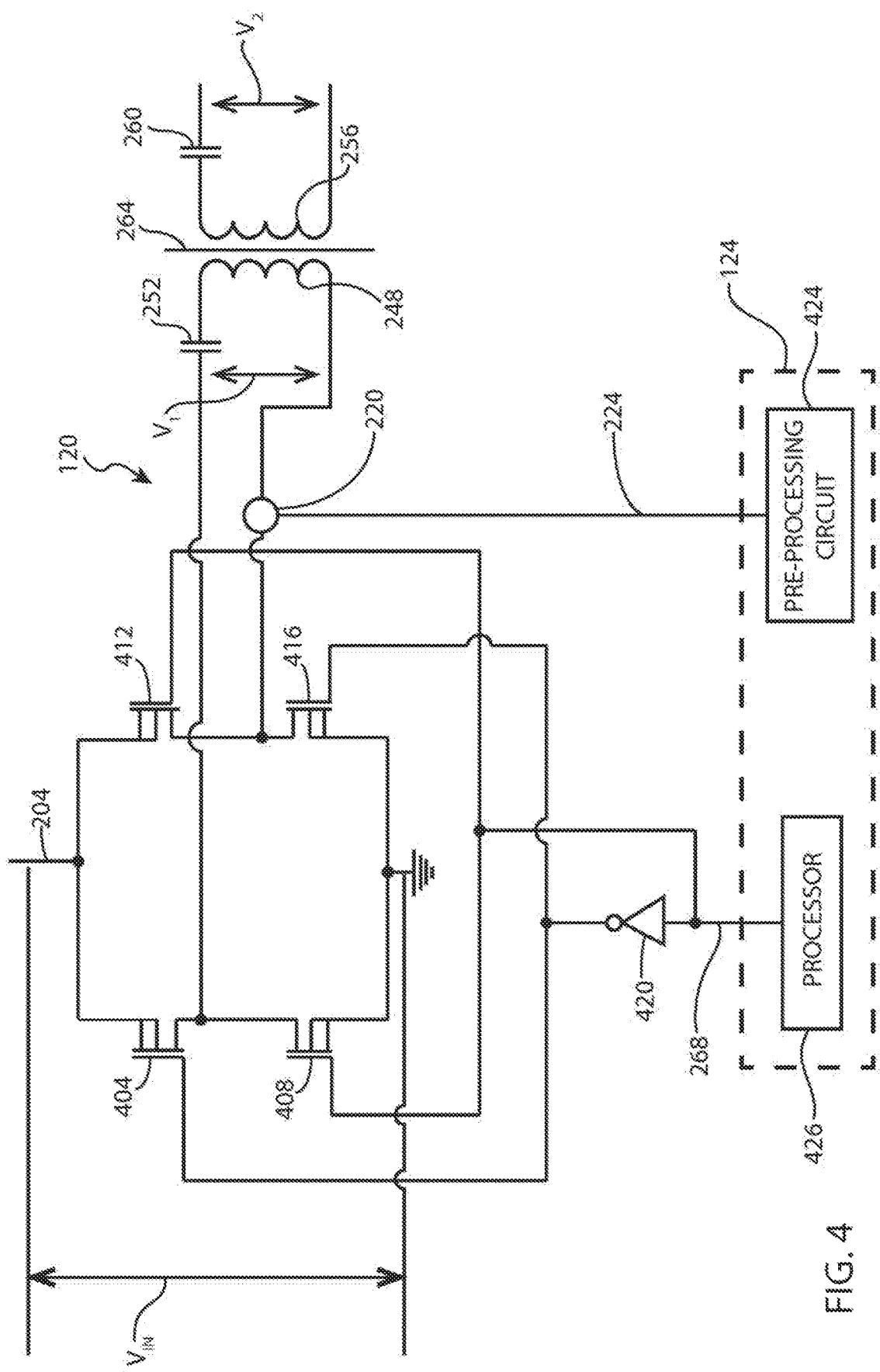
FIG. 4 is a circuit diagram that shows one implementation of the inverter shown in FIG. 1.

FIG. 4 is a circuit diagram that shows one implementation of the inverter 116. As shown in FIG. 4, the inverter 116 may comprise four transistors 404, 408, 412, 416, which may be metal oxide field-effect transistors (MOSFETs), connected in an H-bridge configuration. The four transistors 404, 408, 412, 416 may drive the external coil network 120 through the conductor 212. Each of the transistors 404, 408, 412, 416, may be controlled by a respective high-frequency drive signal provided on the conductor 268, with two of the drive signals being 180° out of phase, or complemented, with respect to the other two via an inverter 420. The drive signals may be 50% duty cycle square waves provided at a frequency of about 200 kHz, for example. Although a particular type of DC-to-AC converter has been described above, any type of electronic switching network that generates a high-frequency voltage may be used. For example, as an alternative to the H-bridge configuration, the inverter 116 may have transistors arranged in a voltage source half bridge configuration or in a current source configuration or in a class-DE amplifier voltage source configuration.

The inverter 116 may be connected to the controller 124 to control the operation of the inverter 116 based on one or more characteristics of the current sensed by the sensor 220. Referring to FIG. 2, the inverter 116 may be connected to the controller 124 through the conductor 268. The controller 124, in turn, may be connected to the current sensor 220 via the line 224. Referring to FIG. 4, controller 124 may include certain pre-processing circuits 424 that operate on the current signal and a processor 426 that receives input generated by the pre-processing circuit 424 based the current signal. The pre-processing circuits 424 may include circuits that accomplish such functions as current to voltage conversion, decoupling detection, interference detection, and shorting/un-shorting detection, and so on.

In one embodiment, the pre-processing circuit 424 may be configured to generate a voltage that is indicative of the magnitude of the electric current flowing through the external coil 248, where the current flowing through the external coil 248 is proportional to the voltage across the internal coil 256. During the idle mode, the shorting switches 272 are closed, which causes the voltage across the internal coil network 128 to significantly decrease. That voltage decrease causes the current in the external coil 248 to be significantly decreased, in accordance with Equation (1). Consequently, the voltage generated by the pre-processing circuit 424 decreases significantly when the power circuit 132 is in the idle mode.

The output of the controller 124 may be configured to drive the inverter 116 at different frequencies depending on the voltage received from the pre-processing circuit 424. In one embodiment, the controller 124 output may be provided by the processor 426, which provides output responsive to input from the pre-processing circuit 424. When the preprocessing circuit 424 generates a voltage that is not decreased indicating that the power circuit 132 is in power supply mode, the output of the controller 124 may drive the inverter 116 at a first frequency, such as 200 kHz. When the pre-processing circuit 424 generates a voltage that is decreased indicating that the power circuit 132 is in idle mode, the output of the controller 124 may drive the inverter 116 at a second frequency that is an odd sub-harmonic of the frequency generated during the power supply mode.

Figure 5:
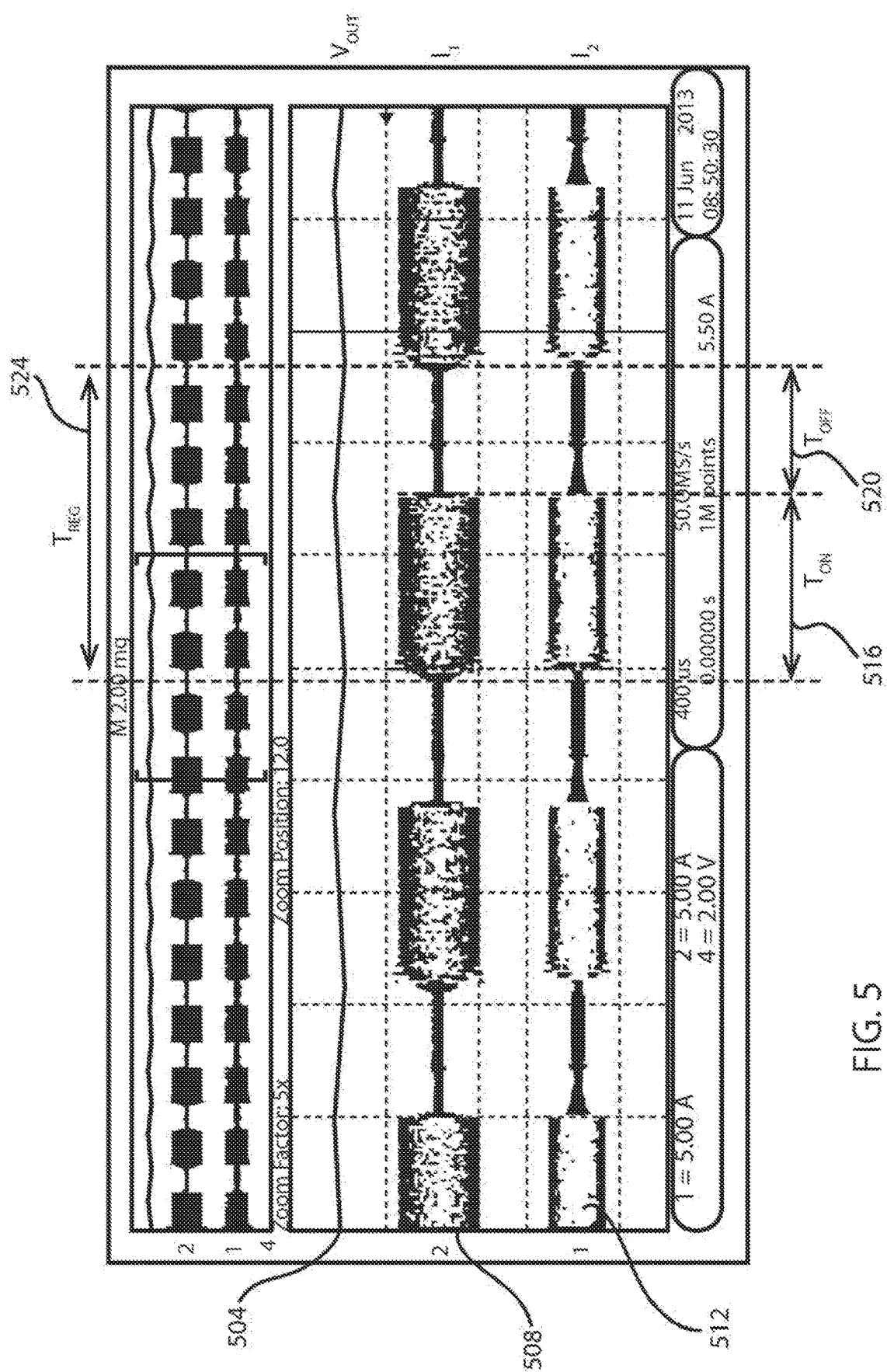
FIG. 5 is an illustration of waveform traces for signals that are present in the system of FIG. 1 as power is transferred between the external assembly and the internal assembly.

FIG. 5 is an illustration of various waveform traces that represent signals that are present in the system 100 as power is transferred between the external assembly 104 and the internal assembly 108. FIG. 5 illustrates the magnitude of the voltage across the power supply capacitor associated with the regulator circuit 144 as this signal changes over time. This voltage is labeled as VOUT and is referred to with reference number 504. As can be seen in FIG. 5, VOUT gradually decreases as current is drawn from the capacitor associated with the regulator circuit 144, and gradually increases when current is supplied to the capacitor from the rectifier 152. The gradual decrease of VouT corresponds to the power circuit 132 being in the idle mode. Similarly, the gradual increase of Vout corresponds to the power circuit 132 being in the power supply mode.

FIG. 5 additionally illustrates a current signal that represents current present in the external coil 248 as power is transferred between the external assembly 104 and the internal assembly 108. This current signal is labeled as Ii and is referred to with reference number 508. The current signal I1 can be generated by the current sensor 220. FIG. 5 also illustrates a current signal that represents current present in the internal coil 256 as power is transferred between the external assembly 104 and the internal assembly 108. This current signal is labeled as I2 and is referred to with reference number 512. As can be seen in FIG. 5, the amplitudes of both Ii and I2 are smaller when the power circuit 132 is in the idle mode as compared to when the power circuit 132 is in the power supply mode. I1 is lower because V2 drops to approximately zero in response to the shorting switches 272 closing so as to short the internal resonant network 128. I2 is lower because V1 drops to a fraction of its power mode value in response to the inverter 116 operating at a sub-harmonic frequency.

Data Communication

Figure 6A:
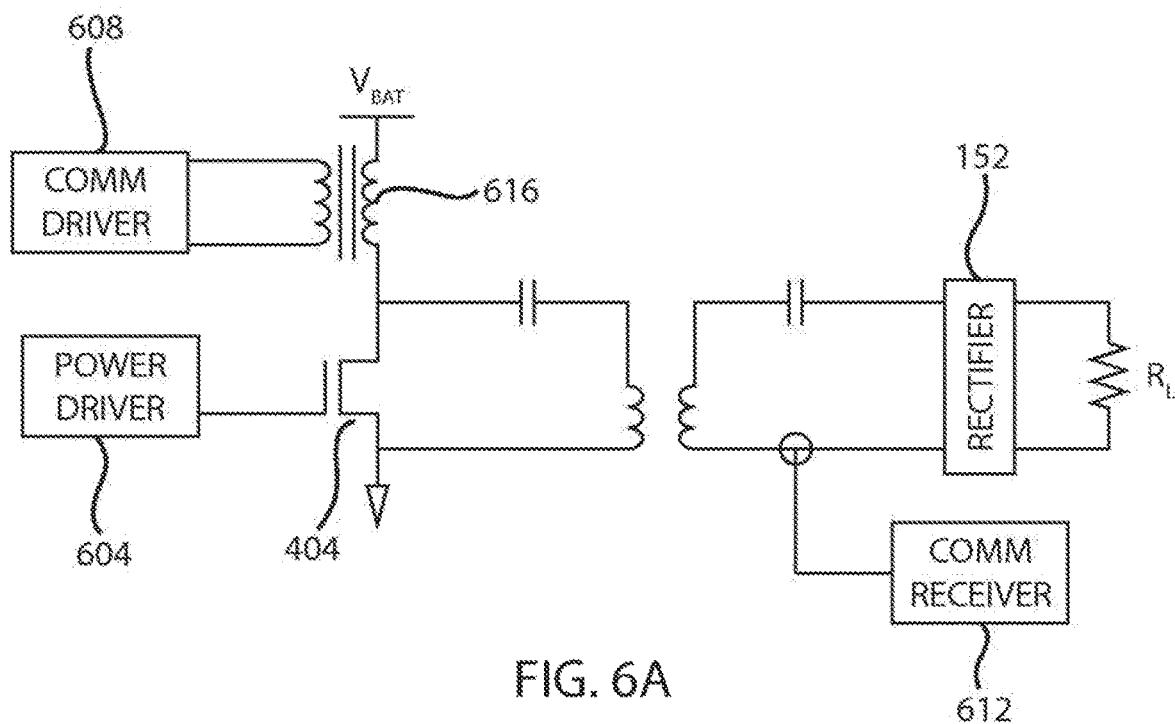
FIGS. 6A-C are simplified circuit diagrams that include mechanisms for affecting data communication in accordance with present embodiments.
Figure 6B:
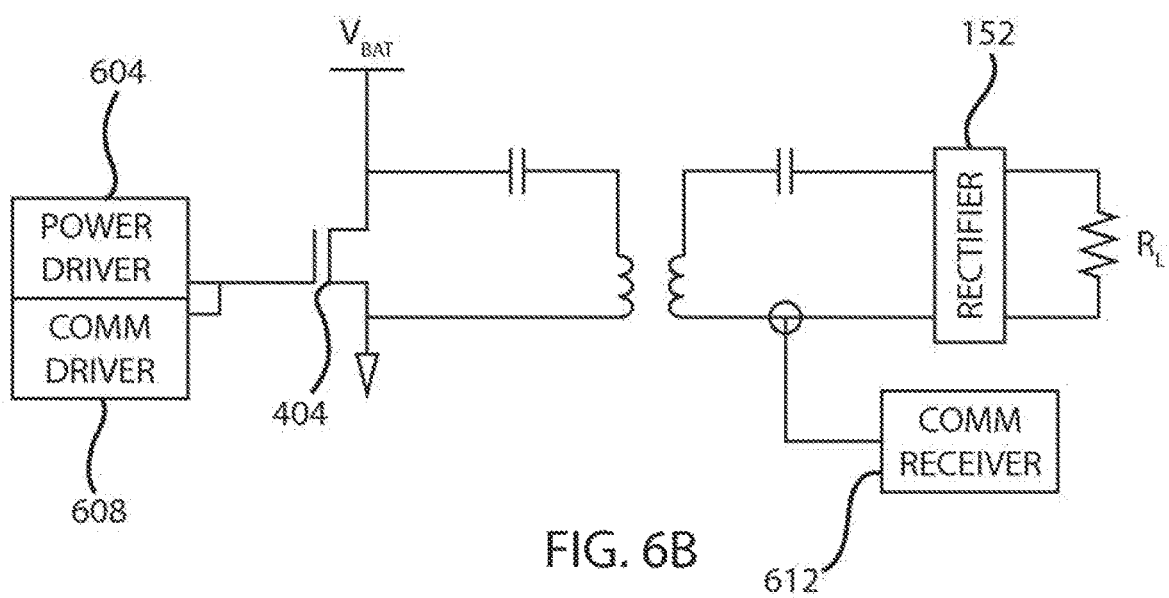
Figure 6C:
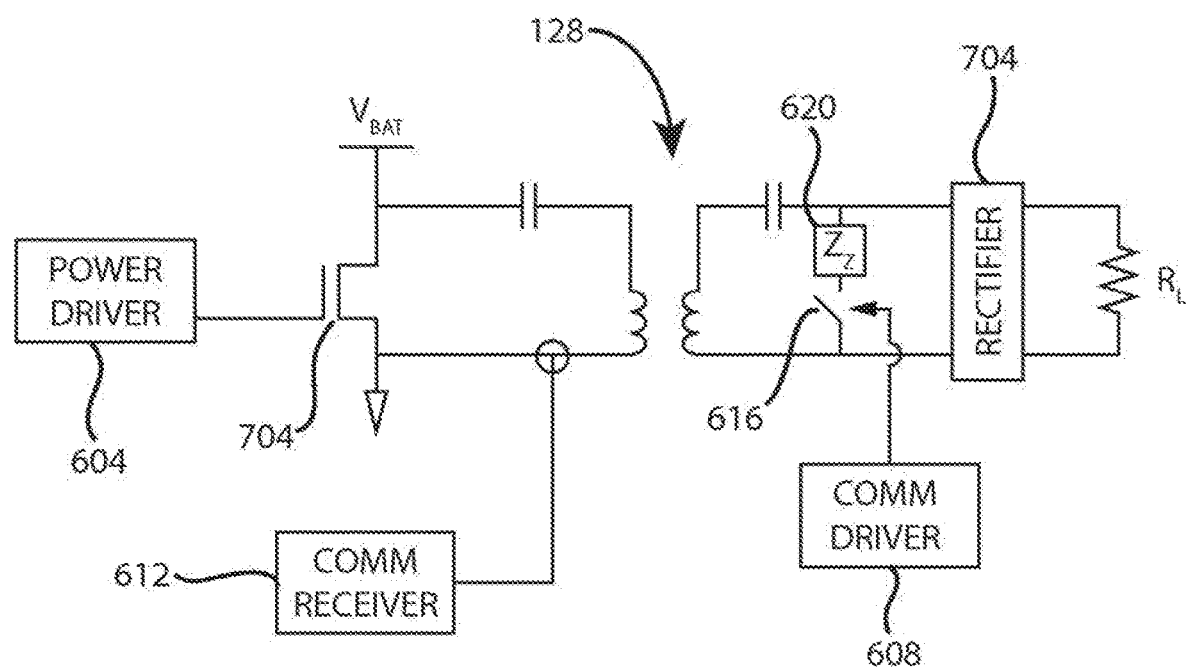

Present embodiments may be configured to transfer data through the skin of the subject within whom the medical device is implanted. The system may be configured to transfer data from the external primary to the implanted secondary, from the implanted secondary to the external primary, or both. FIGS. 6A-C are simplified diagrams that include mechanisms for affecting this kind of data transfer. Certain components illustrated in other figures are omitted from FIGS. 6A-C to simplifying the drawings. Specifically, FIGS. 6A-C shows a rectifier 152, while other components of the internal assembly 108 are omitted. Similarly, FIGS. 6A-C shows a power driver 604 and a power transistor 404, while other components of the external assembly 104 are omitted. The power driver 604 may be a controller 124 or other component that drives the various transistors associated with the inverter 116, as described above in connection with FIG. 4. Only one transistor 404 is shown in FIGS. 6A-C in order to simplify the drawing. In addition to these components, FIGS. 6A-C also shows a communication driver 608 that is configured to transmit a data signal through the skin 264 of the subject. In FIGS. 6A-B, the communication driver 608 is located on the primary side and is configured to transmit a data signal that is received at the implanted secondary. In FIG. 6C, the communication driver 608 is located on the secondary side and is configured to transmit a data signal that is received at the external primary.

Turning first to data transmission from the external primary to the implanted secondary, reference is made to FIGS. 6A-B. Here, the communication driver 608 is connected to the transistor 404 and is configured to encode a data signal into the power signal output by the transistor 404. In order to transmit data, the communication driver 608 may modulate an attribute of the power signal as power is transferred from the external primary to the implanted secondary. Attributes of the power signal that the communication driver 608 may modulate include the amplitude, the frequency, and/or the phase. Once the power signal as modulated by the communication driver 608 is received at the implanted secondary, the power signal may be demodulated by a communication receiver 612 so as to extract the data signal. The communication driver 608 may operate to transmit the data signal through the skin of the patient during either the power mode or the idle mode.

FIG. 6A shows an implementation where the communication driver 608 is connected to the drain of the power transistor 404 through a transformer 616. The primary side of the transformer 616 may be connected to the communication driver 608. The secondary side of the transformer 616 connects the DC power source to the drain or the high side of the power transistor 404. Through this connection to the transistor 404, the communication driver 608 may modulate the power signal output from the transistor 404.

FIG. 6B shows an implementation where the communication driver 608 is connected to or otherwise associated with the power driver 604. In this configuration, the communication driver 608 alters the output of the power driver so as to modulate the power signal output from the transistor 404. Specifically, the communication driver 608 modulates the drive signal output from the power driver 604. The modulated drive signal is then received as input at the transistor 404, which then outputs a modulated power signal.

Figure 7:
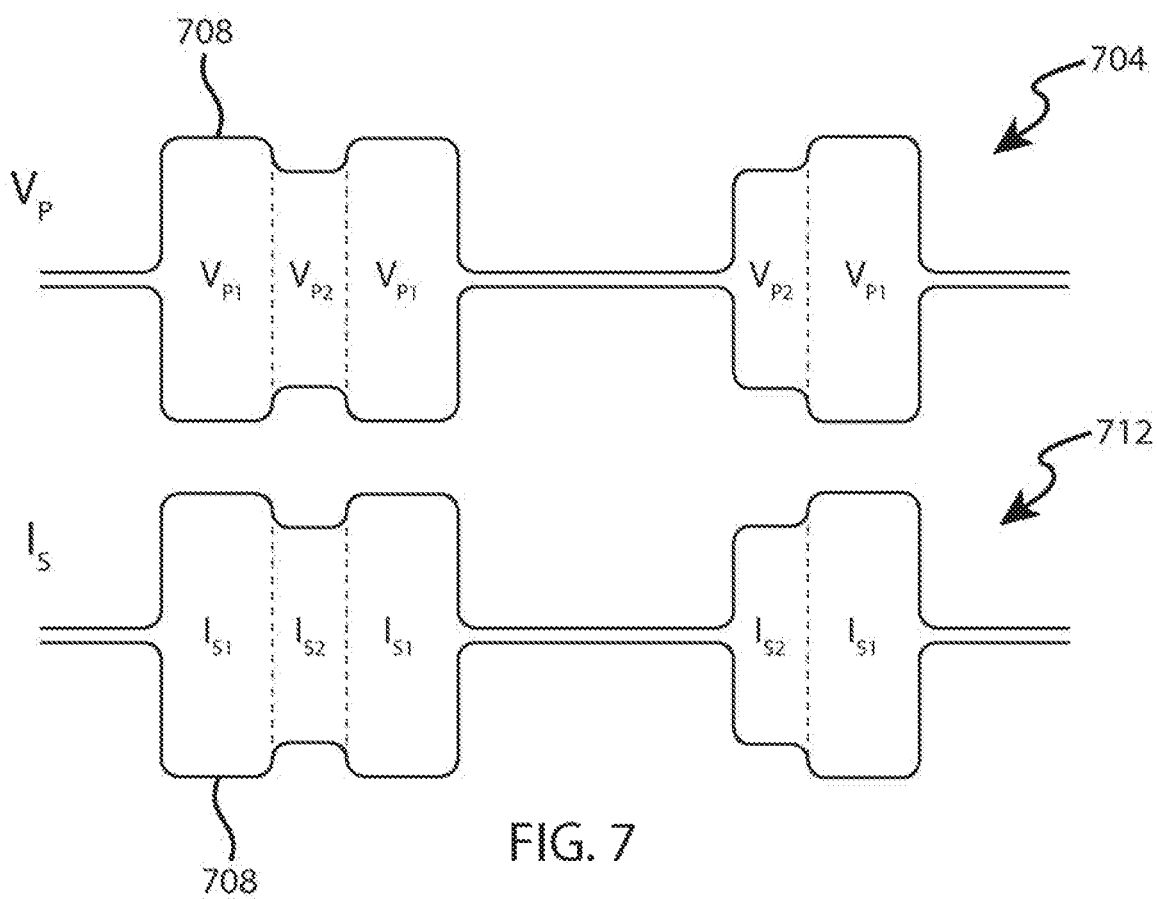
FIG. 7 is an illustration of example signal traces that show an amplitude modulation in accordance with present embodiments.

As mentioned, the communication driver 608 may transmit data by modulating the amplitude of the power signal that is output from the power transistor 404. The communication driver 608 may modulate the amplitude of the power signal while the system 100 is operating in either the power supply mode or in the idle mode. FIG. 7 is an illustration of example signal traces that show an amplitude modulation by the communication driver 608. By way of example and not limitation, FIG. 7 shows an amplitude modulation that occurs when the system is operating in power supply mode. FIG. 7 shows a primary side voltage signal 704 encoded with a plurality of symbols 708 represented by different signal amplitudes. The different signal amplitudes are injected into the primary side voltage signal 704 through the operation of the communication driver 608. Specifically, in the configuration of FIG. 6A, different signal amplitudes may be coupled into the power signal through the transformer 616. In the configuration of FIG. 6B, different signal amplitudes may be produced by the power driver 604 being driven by different amounts. In either case, the primary voltage signal 704 induces the current signal 712 in the secondary. Here, the encoded data signal is also transmitted to the secondary. Thus, as can be seen in FIG. 7, the secondary side current signal 712 is encoded with a plurality of symbols 708 represented by the different signal amplitudes. The secondary side signal 712 may be received at the communication receiver 612, which may demodulate the signal 712 so as to extract the encoded data represented by the various symbols 708.

Figure 8A:
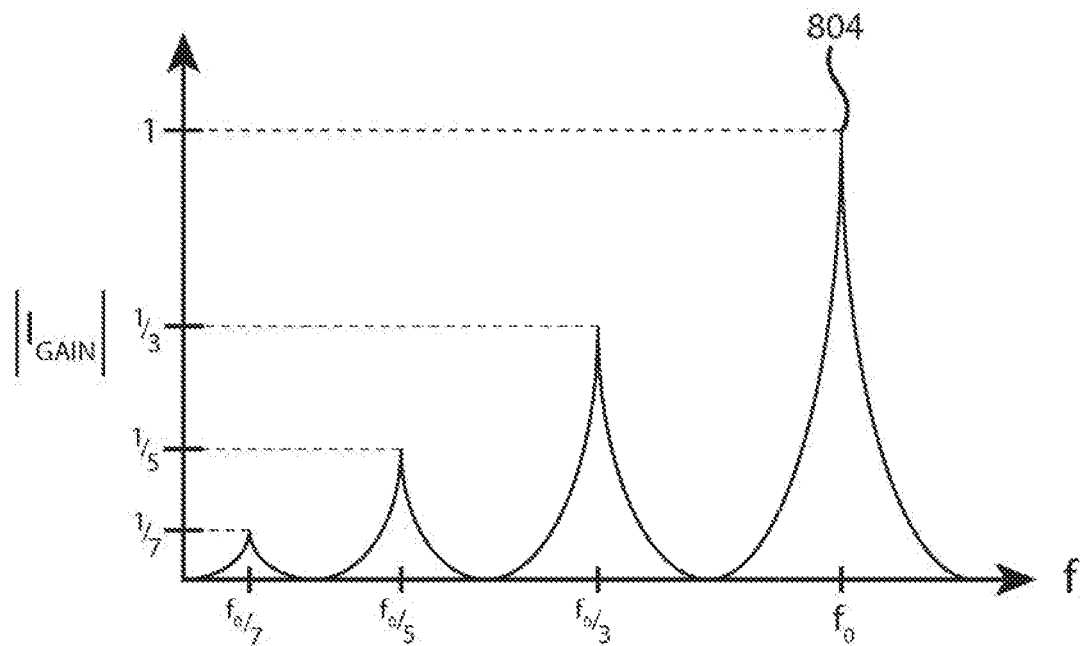
FIG. 8A is an illustration of the secondary current gain response to the communication driver's use of subharmonic frequencies.
Figure 8B:
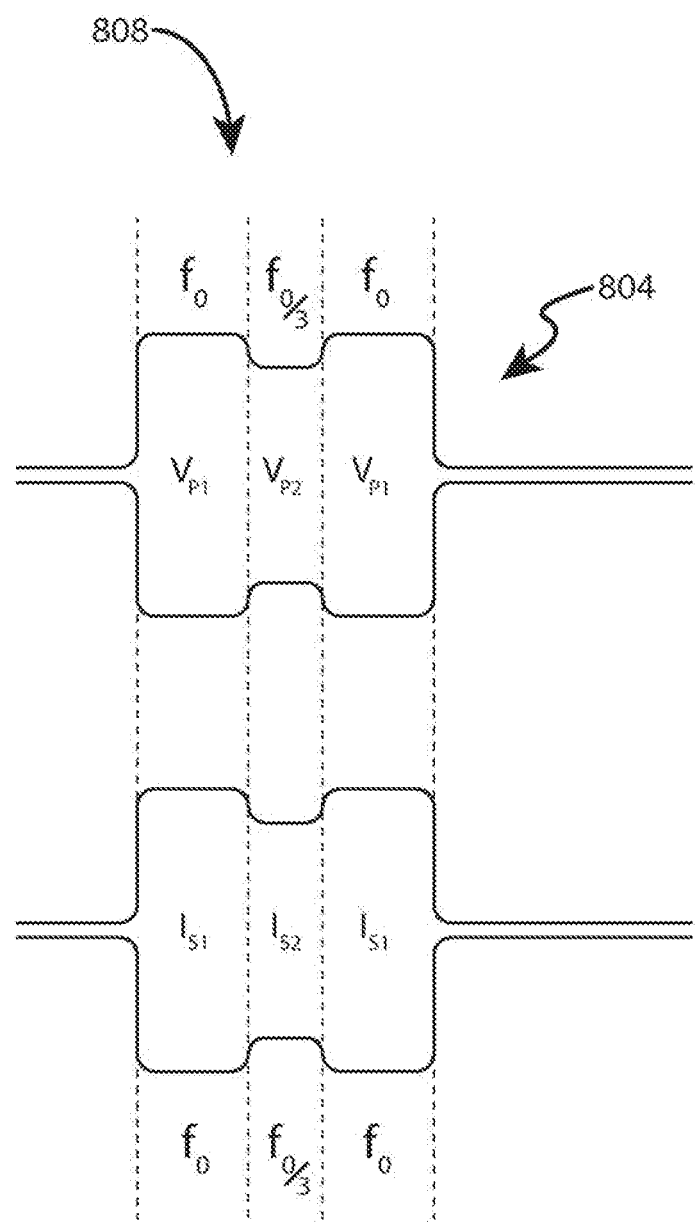
FIG. 8B is an illustration of a primary side voltage signal encoded with a plurality of symbols that correspond to different subharmonics.

In the configuration of FIG. 6B, the communication driver 608 may also indirectly modulate the amplitude of the power signal by shifting the power signal among different subharmonics of the fundamental drive frequency. FIG. 8A is an illustration of the secondary current gain response to the communication driver's 608 use of subharmonic frequencies. FIG. 8B shows a primary side voltage signal 804 encoded with a plurality of symbols 808 that correspond to different subharmonics. The primary side voltage signal 804 is driven at different subharmonics by an operation of the communication driver 608 that modifies the output of the power driver 604. As shown in FIG. 8B, the primary voltage signal 804 induces a current signal in the secondary, which also transmits the encoded data to the secondary. This secondary side current signal may be received at the communication receiver 612, which may demodulate the signal so as to extract the encoded data.

Figure 9:
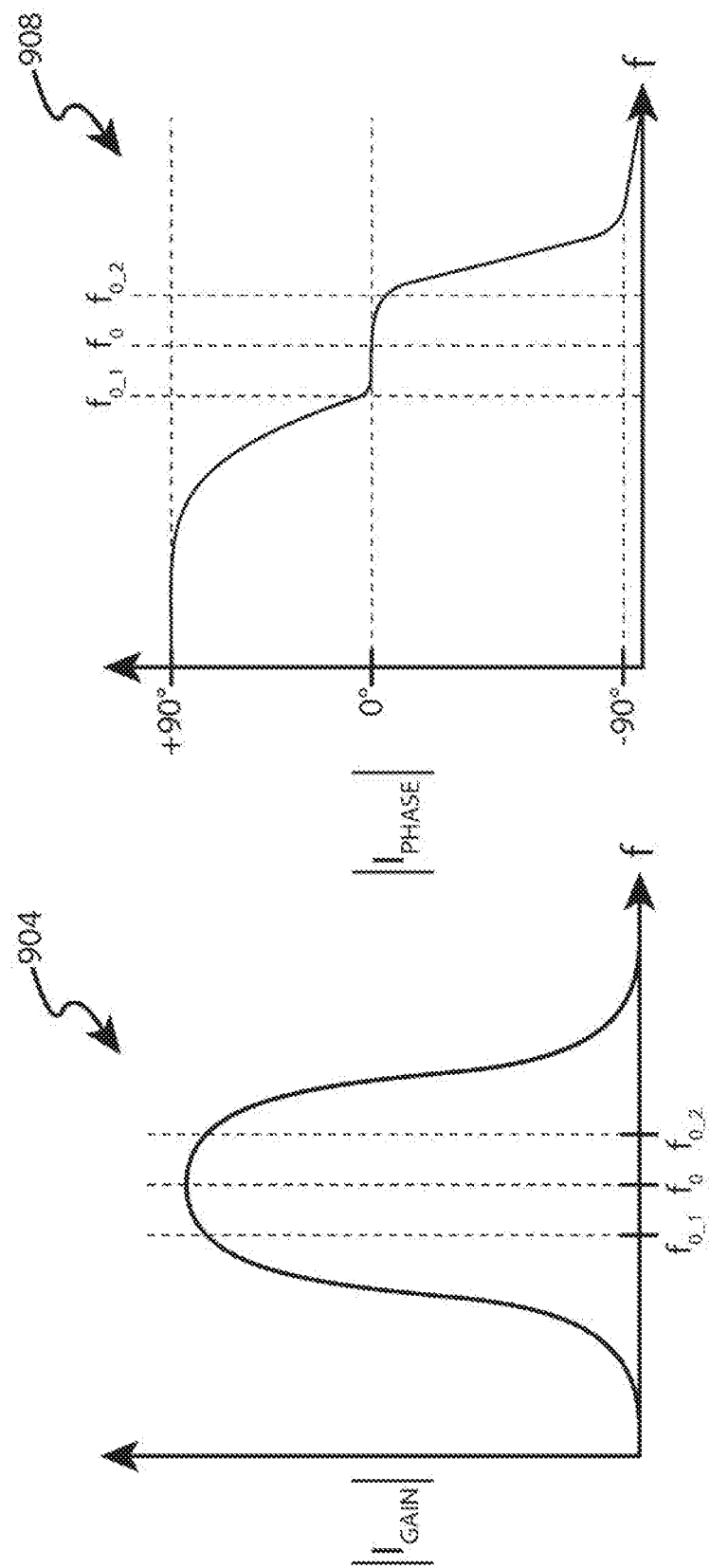
FIG. 9 is a graph of the frequency response of an example system in accordance with embodiment discussed herein.

In the configuration of FIG. 6B, the communication driver 608 may also transmit data by modulating the frequency of the power signal that is output from the power transistor 404. FIG. 9 is a graph of the frequency response of an example system 100 in accordance with embodiment discussed herein for power supply mode. FIG. 9 includes a first plot 904 of gain versus frequency, and a second plot 908 of phase versus frequency for the example system 100. FIG. 9 shows a relatively wide bandwidth. Specifically, as operating frequency is changed the system's 100 gain and phase remains substantially the same. The system can support about 20 kHz of variance before the system starts to exhibit any major changes to performance. Thus, the communication driver 608 can encode data into the inductive channel between the primary and secondary by dithering the operating frequency about +/−10 kHz around a nominal frequency. The communication driver 608 may modulate the frequency of the power signal while the system 100 is operating in either the power supply mode or in the idle mode.

Figure 10:
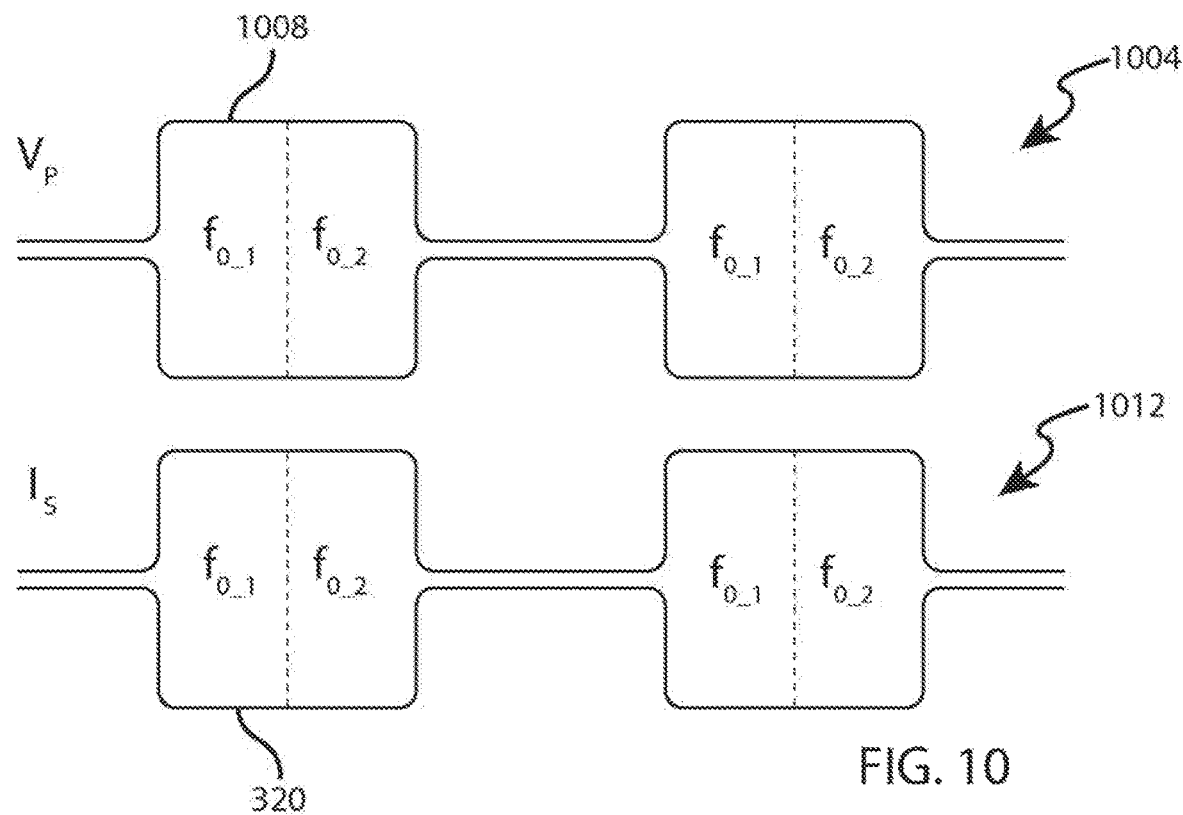
FIG. 10 is an illustration of example signal traces that show a frequency modulation in accordance with present embodiments.

FIG. 10 is an illustration of example signal traces that show a frequency modulation by the communication driver 608. By way of example and not limitation, FIG. 10 shows a frequency modulation that occurs when the system is operating in power supply mode. FIG. 10 shows a primary side voltage signal 1004 encoded with a plurality of symbols 1008 represented by different signal frequencies. The different signal frequencies are injected into the primary side voltage signal 1004 through the operation of the communication driver 608. Specifically, in the configuration of FIG. 6B, different signal frequencies may be produced by the power driver 604 being driven by different amounts. The primary voltage signal 1004 induces the current signal 1012 in the secondary. Here, the encoded data signal is also transmitted to the secondary. Thus, as can be seen in FIG. 10, the secondary side current signal 1012 is encoded with a plurality of symbols 1008 represented by the different signal frequencies. The secondary side signal 1012 may be received at the communication receiver 612, which may demodulate the signal 1012 so as to extract the encoded data represented by the various symbols 1008.

The communication driver 608 may also transmit data by modulating the phase of the power signal that is output from the power transistor 404. As mentioned, the system alternates between a power supply mode and an idle mode. During the idle mode, the inductive link between the primary and the secondary is shut off at least for a short period of time. Because of this shut-off, consecutive power modes are not synchronized. Thus, phase information can be varied from one power cycle to another by the communication driver 608. In this way, phase information of the signal in the power supply mode can be used to transmit data.

Figure 11:
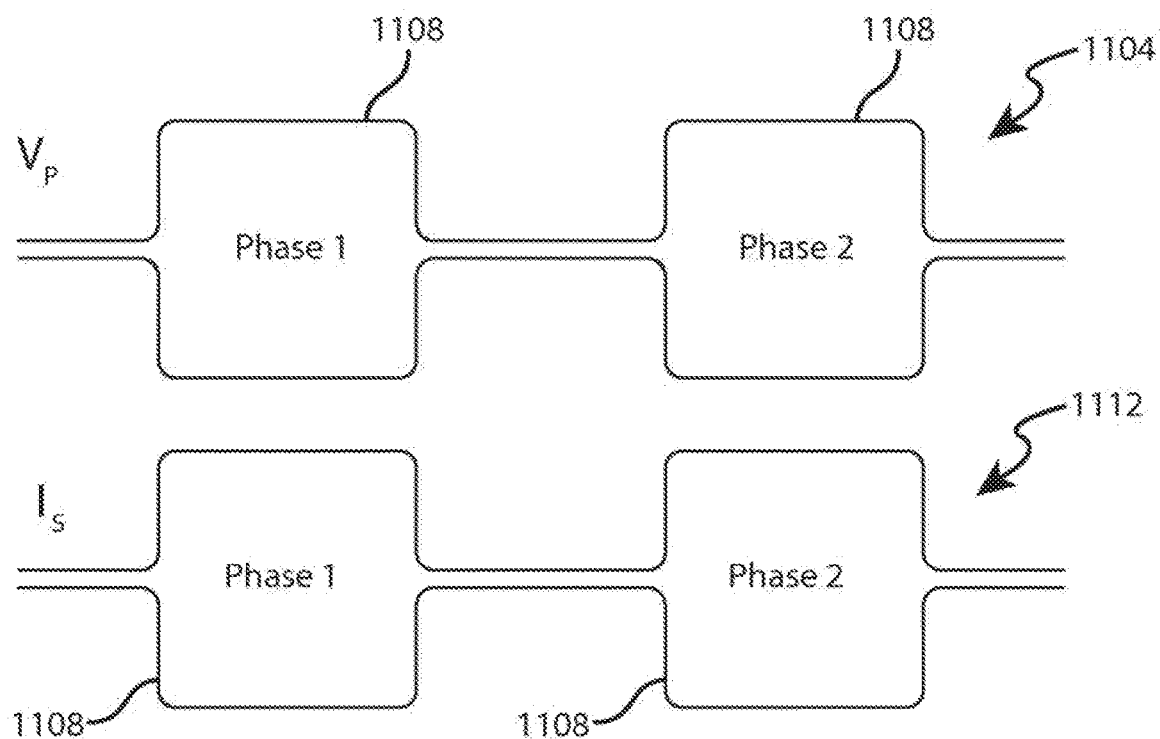
FIG. 11 is an illustration of example signal traces that show a phase modulation in accordance with present embodiments.

FIG. 11 is an illustration of example signal traces that show a phase modulation by the communication driver 608. FIG. 11 shows a primary side voltage signal 1104 encoded with a plurality of symbols 1108 represented by different phase angles. The different phase angles are injected into the primary side voltage signal 1104 through the operation of the communication driver 608. Specifically, for each power cycle, the communication driver 608 sets the phase angle for the primary side voltage signal 1104. The primary voltage signal 1104 induces the current signal 1112 in the secondary. Here, the encoded data signal is also transmitted to the secondary. Thus, as can be seen in FIG. 11, over a plurality of power cycles, the secondary side current signal 1112 is encoded with a plurality of symbols 1108 represented by the different phase angles. The secondary side signal 1112 may be received at the communication receiver 612, which may demodulate the signal 1112 over a plurality of power cycles so as to extract the encoded data represented by the various symbols 1108.

Communicating data from the external primary to the implanted secondary as discussed above, is referred to herein as "upstream" data communication. Examples of "downstream" communication where data is communicated from the implanted secondary to the external primary are provided in the following United States patents, the entirety of which patents are hereby incorporated by reference: U.S. Pat. Nos. 6,579,315; 6,478,820; 6,458,164; and 6,451,055. Generally, these patents include disclosure of downstream communication embodiments that use amplitude shift keying, or amplitude modulation, from the secondary to the primary during a power supply mode portion of a power cycle. Not disclosed in these patents, but disclosed herein are system and methods for communicating data downstream during the idle mode portion of the power cycle. Specifically, data may be communicated from the implanted secondary to the external primary during the idle mode using amplitude or phase modulation. In addition, data may be communicated downstream using load modulation during a power supply mode portion of a power cycle.

FIG. 6C is a simplified circuit diagram that includes a mechanism for affecting data transfer from the implanted secondary to the external primary. Here, the communication driver 608 is connected to the internal resonant network 128 through a switch 616, which in turn, is connected to a load element 620. In an open position, the switch 616 couples the load element 620 into the internal resonant network 128. When the switch 616 is in the closed position, the load element 620 is decoupled from internal resonant network 128. In the configuration of FIG. 6C, the communication driver 608 encodes a data signal into the power transfer that is occurring across the inductive link between the primary and the secondary. Specifically, the communication driver 608 modulates the electrical load presented by the implanted secondary by switching the load element 620 in and out of the internal resonant network 128

Present embodiments make use of the fact that, in the idle mode, the primary 120 and secondary resonant networks 128 do not exchange significant amount of power and are free to exchange data with minimal detriment to power transfer. Thus, in the idle mode, the secondary resonant network 128 can be modulated to reflect impedance changes back to the primary. In one embodiment, the load element 620 is resistive and impedance changes are reflected back to the primary by resistive loading of the secondary resonant network 128. Here, data communication is achieved by switching in and out a small resistor into the secondary resonant network 128. As a result, the resistive loading is reflected in the primary current. In other embodiments the load element 620 is reactive and the system implements reactive loading of the secondary resonant network 128. Here, data communication is achieved by switching in and out a small reactive component, (such as a capacitor) into the secondary resonant network 128. As a result, the reactive loading will be reflected in primary current due to gain or phase change.

In accordance with embodiments discussed herein, both "upstream" and "downstream" communication may occur in the system 100. Stated another way, the system 100 may implement two way data communication. Here, the power transfer signal or the channel between the primary and the secondary may be modulated by a first and second data signal, where the first signal is encoded at the primary and received at the secondary, and the second signal is encoded at the secondary and received at the primary. In some implementations, the first and second data signals are time multiplexed such each is transmitted during its own dedicated time interval. In other embodiments, the first and second data signals are transmitted simultaneously. It has been found that upstream amplitude modulation can be transmitted simultaneously with downstream amplitude modulation. Upstream frequency modulation can be transmitted simultaneously with downstream amplitude modulation. Similarly, upstream phase modulation be transmitted simultaneously with downstream amplitude modulation.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

The invention claimed is:

1. A system for communicating data in an transcutaneous energy transfer system that includes an external primary and an implantable secondary, comprising:
the external primary including:
a direct current power source;
a resonant circuit;
a power transistor connected to the resonant circuit and configured to drive the resonant circuit with a first time-varying electrical signal having a frequency;
a power driver connected to the power transistor and configured to set the frequency of the first time-varying electrical signal to a resonant frequency to enable transfer of electrical power from the external primary to the implantable secondary; and
a communication driver operatively connected to the power transistor;
a transformer having a primary side that is connected to the communication driver and a secondary side that is coupled in series between the direct current power source and a drain of the power transistor;
wherein the communication driver is configured to encode the first time-varying electrical signal with a data signal by modulating an attribute of the first time-varying electrical signal through the transformer as the electrical power is transferred from the external primary to the implanted secondary; and
the implantable secondary including a communication receiver that is configured to receive the data signal from the external primary;
wherein the communication receiver is configured to convert a secondary time-varying electrical signal induced in the implantable secondary by the first time-varying electrical signal by demodulating the secondary time-varying electrical signal as the electrical power is transferred from the external primary to the implantable secondary.

2. The system of claim 1, wherein the communication driver is further configured to indirectly modulate an amplitude of the first time-varying electrical signal by adjusting a frequency of an output of the power driver to a subharmonic of a fundamental drive frequency.

3. The system of claim 1, wherein the communication driver is further configured to encode the first time-varying signal with the data signal by modulating the frequency of the first time-varying electrical signal.

4. The system of claim 1, wherein the communication driver is further configured to encode the first time-varying signal with the data signal by modulating a phase of the first time-varying electrical signal.

5. The system of claim 1, wherein:
the power driver is configured to alternate the electrical power transfer between a power supply mode and an idle mode responsive to a received indication of power consumption in the implantable secondary; and
the communication driver is further configured to encode the first time-varying signal with the data signal by modulating the attribute of the first time-varying electrical signal during the power supply mode.

6. The system of claim 1, wherein:
the power driver is configured to alternate the electrical power transfer between a power supply mode and an idle mode responsive to a received indication of power consumption in the implantable secondary; and
the communication driver is further configured to encode the first time-varying signal with the data signal by modulating the attribute of the first time-varying electrical signal during the idle mode.

7. An apparatus for communicating data in an transcutaneous energy transfer system that includes an external primary and an implantable secondary, comprising
the external primary;
a resonant circuit coupled to the external primary;
a direct current power source;
a power transistor coupled to the resonant circuit and configured to cause the resonant circuit to provide a first time-varying electrical signal having a frequency;
a power driver coupled to the power transistor and configured to control the frequency of the first time-varying electrical signal to enable power transfer from the external primary to the implantable secondary;
a communication driver coupled to the power transistor and configured to encode the first time-varying electrical signal with a data signal by modulating an attribute of the first time-varying electrical signal; and a transformer having a primary side coupled to the communication driver and a secondary side configured to couple the direct current power source to the power transistor, the secondary side coupled in series between the direct current power supply and a drain of the power transistor;

wherein the communication driver is configured to control the transformer to modulate the attribute of the first time-varying electrical signal.

8. The apparatus of claim 7, wherein the attribute of the first time-varying electrical signal modulated by the communication driver includes an amplitude.

9. The apparatus of claim 7, wherein the communication driver is configured to adjust a frequency of an output of the power driver to a subharmonic of a fundamental drive frequency to modulate the attribute of the first time-varying electrical signal.

10. The apparatus of claim 7, wherein the attribute of the first time-varying electrical signal modulated by the communication driver includes at least one of the frequency or the phase of the first time-varying electrical signal.

11. The apparatus of claim 7, wherein the power driver is configured to alternate the electrical power transfer between a power supply mode and an idle mode responsive to an indication of power consumption of the implantable secondary received from the implantable secondary.

12. The apparatus of claim 11, wherein the communication driver is configured to encode the first time-varying signal with the data signal during the power supply mode.

13. The apparatus of claim 11, wherein the communication driver is configured to encode the first time-varying signal with the data signal during the idle supply mode.

* * * * *